US011531036B2

(12) United States Patent
Dalli et al.

(10) Patent No.: US 11,531,036 B2
(45) Date of Patent: Dec. 20, 2022

(54) METHOD AND APPARATUS FOR DETERMINING THE EFFICACY OF STATINS FOR TREATING INFLAMMATORY DISEASES IN INDIVIDUAL PATIENTS

(71) Applicant: Queen Mary University of London, London (GB)

(72) Inventors: Jesmond Dalli, London (GB); Romain Alexandre Colas, London (GB); Patricia Regina Soares De Souza, London (GB); Mary Elizabeth Walker, London (GB)

(73) Assignee: Queen Mary University of London, London (GB)

( * ) Notice: Subject to any disclaimer, the term of this patent is extended or adjusted under 35 U.S.C. 154(b) by 227 days.

(21) Appl. No.: 16/608,428

(22) PCT Filed: Apr. 26, 2018

(86) PCT No.: PCT/EP2018/060813
§ 371 (c)(1),
(2) Date: Oct. 25, 2019

(87) PCT Pub. No.: WO2018/197650
PCT Pub. Date: Nov. 1, 2018

(65) Prior Publication Data
US 2020/0191807 A1    Jun. 18, 2020

(30) Foreign Application Priority Data
Apr. 27, 2017  (GB) ..................... 1706747

(51) Int. Cl.
*G01N 33/92*     (2006.01)
*G01N 33/543*    (2006.01)
*A01N 1/02*      (2006.01)

(52) U.S. Cl.
CPC .......... *G01N 33/92* (2013.01); *A01N 1/0284* (2013.01); *G01N 33/54366* (2013.01); *G01N 2800/102* (2013.01); *G01N 2800/32* (2013.01); *G01N 2800/52* (2013.01)

(58) Field of Classification Search
CPC ............ G01N 33/92; G01N 2800/102; G01N 2800/32; G01N 2800/52
See application file for complete search history.

(56) References Cited

FOREIGN PATENT DOCUMENTS

| WO | 2002024194 | 3/2002 |
|----|------------|--------|
| WO | 2007127377 | 11/2007 |
| WO | 2009053523 | 4/2009 |
| WO | 2011116128 | 9/2011 |
| WO | 2014193652 | 12/2014 |
| WO | 2017015271 | 1/2017 |
| WO | 2018197650 | 11/2018 |

OTHER PUBLICATIONS

Inflamm. Bowel Dis 2016 22:724-732 (Year: 2016).*
Bioorganic & Medicinal Chemistry Letters 2017 27: 2259-2266 (Year: 2017).*
Birnbaum et al., "Augmentation of Myocardial Production of 15-Epi-Lipoxin-A4 by Pioglitazone and Atorvastatin in the Rat", Circulation, 2006, 114, pp. 929-935.
Walker et al., "13-Series resolvins mediate the leukocyte-platelet actions of atorvastatin and pravastatin in inflammatory arthritis", The FASEB Journal, 2017, 31(8), pp. 3636-3648.
Dalli et al., "Specific lipid mediator signatures of human phagocytes: microparticles stimulate macrophage efferocytosis and pro-resolving mediators", Blood, 2012, 120(15), pp. e60-e72.
Superko et al., "Statins personalized", Med Clin North Am, 2012, 96(1), pp. 123-139.
Yang et al., "Metabolomics-Lipidomics of Eicosanoids and Docosanoids Generated by Phagocytes", Current Protocols in Immunology, 2011, 95(1), pp. 14.26.1-14.26.26.
Chin et al., "Commercialization of microfluidic point-of-care diagnostic devices", Lab Chip, 2012, 12(12), pp. 2118-2134.
Gittens et al., "Methods for Assessing the Effects of Galectins on Leukocyte Trafficking", Methods Mol Biol, 2015, 1207, pp. 133-151.
Rathod et al., "Accelerated resolution of inflammation underlies sex differences in inflammatory responses in humans", J Clin Invest, 2017, 127(1), pp. 169-182.
Chin et al., "Microfluidics-based diagnostics of infectious diseases in the developing world", Nature Medicine, 2011, 17, pp. 1015-1019.
Colas et al., "Identification and signature profiles for pro-resolving and inflammatory lipid mediators in human tissue", Am J Physiol Cell Physiol, 2014, 307, pp. C39-C54.
Planaguma et al., "Lovastatin decreases acute mucosal inflammation via 15-epi-lipoxin A 4", Mucosal Immunol, 2010, 3(3), pp. 270-279.
Dalli et al., "Elucidation of novel 13-series resolvins that increase with atorvastatin and clear infections", Nature Medicine, 2015, 21(9). pp. 1071-1075.

(Continued)

*Primary Examiner* — Changhwa J Cheu
(74) *Attorney, Agent, or Firm* — Armstrong Teasdale LLP

(57) ABSTRACT

A method, device, computer program and related immunoassay are disclosed for assessing the efficacy of a statin selected from, for example, selected from RvT1 (7,13,20-trihydroxy-8,10,14,16Z,18-docosapentaenoic acid), RvT2 (7,12,13-trihydroxy-8,10,14,16Z,19Z-docosapentaenoic acid), RvT3 (7,8,13-trihydroxy-9,11,14,16Z,19Z-docosapentaenoic acid) and RvT4 (7,13-dihydroxy-8,10,14,16Z,19Z-docosapentaenoic acid), for use in the treatment of an inflammatory condition in an individual patient, which comprises measuring the levels of at least one 13-series resolvin in biological samples obtained from the patient before and after administration of the statin, wherein an increase in the level of the resolvin after administration of the statin is indicative of efficacy of the statin. Also disclosed is a method of storing a biological sample to preserve lipid mediators in the sample comprising placing the sample in an organic solvent and storing the sample at a temperature of ≤−75° C.

12 Claims, 17 Drawing Sheets

(56) References Cited

OTHER PUBLICATIONS

Norling et al., "Proresolving and cartilage-protective actions of resolvin D1 in inflammatory arthritis", JCI Insight, 2016, 1(5), pp. e85922.
Abdulnour et al., "Aspirin-triggered resolvin D1 is produced during self-resolving gram-negative bacterial pneumonia and regulates host immune responses for the resolution of lung inflammation", Mucosal Immunol, 2016, 9 (5), pp. 1278-1287.
Akagi et al., "Systemic delivery of proresolving lipid mediators resolvin D2 and maresin 1 attenuates intimal hyperplasia in mice", FASEB J, 2015, 29(6), pp. 2504-2513.
Akiba et al., "Involvement of lipoxygenase pathway in docosapentaenoic acid-induced inhibition of platelet aggregation", Biol Pharm Bull, 2000, 23, pp. 1293-1297.
Arnardottir et al., "Resolvin D3 Is Dysregulated in Arthritis and Reduces Arthritic Inflammation", J Immunol, 2016, 197(6), pp. 2362-2368.
Brancaleone et al., "A vasculo-protective circuit centered on lipoxin A4 and aspirin-triggered 15-epi-lipoxin A4 operative in murine microcirculation", Blood, 2013, 122(4), pp. 608-617.
Chatterjee et al., "The pro-resolving lipid mediator maresin 1 (MaR1) attenuates inflammatory signaling pathways in vascular smooth muscle and endothelial cells", PLoS One, 2014, 9(11), pp. e113480.
Colas et al., "Impaired Production and Diurnal Regulation of Vascular RvD(n-3 DPA) Increase Systemic Inflammation and Cardiovascular Disease", Circulation Research, 2018, 122(6), pp. P855-P863.
Dalli et al., "Novel n-3 Immunoresolvents: Structures and Actions", Scientific Reports, 2013, 3(1), pp. 8-9.
Dalli et al., "Vagal Regulation of Group 3 Innate Lymphoid Cells and the Immunoresolvent PCTR1 Controls Infection Resolution", Immunity, 2017, 46(1), pp. 92-105.
Dalli et al., "Human Sepsis Eicosanoid and Proresolving Lipid Mediator Temporal Profiles: Correlations With Survival and Clinical Outcomes", Crit Care Med, 2017, 45(1), pp. 58-68.
Dominguez-Rodriguez et al., "Inflammatory Systemic Biomarkers in Setting Acute Coronary Syndromes—Effects of the Diurnal Variation", Current Drug Targets, 2009, 10(10), pp. 1001-1008.
Dona et al., "Resolvin E1, an EPA-derived mediator in whole blood, selectively counter-regulates leukocytes and platelets", Blood, 2008, 112(3), pp. 848-855.
El Kebir et al., "Resolvin E1 promotes phagocytosis-induced neutrophil apoptosis and accelerates resolution of pulmonary inflammation", Proc Natl Acad Sci USA, 2012, 109(37), pp. 14983-14988.
Fredman et al., "An imbalance between specialized pro-resolving lipid mediators and pro-inflammatory leukotrienes promotes instability of atherosclerotic plaques", Nat Commun, 2016, 7, pp. 12859.
Furman et al., "Circulating monocyte-platelet aggregates are an early marker of acute myocardial infarction", J Am Coll Cardiol, 2001, 38(4), pp. 1002-1006.
Gilbert et al., "Resolvin D1 Reduces Infarct Size Through a Phosphoinositide 3-Kinase/Protein Kinase B Mechanism", J Cardiovasc Pharmacol, 2015, 66(1), pp. 72-79.
Gobbetti et al., "Protectin D1 n-3 DPA and resolvin DS n _3 n-3 DPA are effectors of intestinal protection", Proc Natl Acad Sci USA, 2017, 114(15), pp. 3963-3968.
Helgadottir et al., "Association between the gene encoding 5-lipoxygenase-activating protein and stroke replicated in a Scottish population", Am J Hum Genet, 2005, 76(3), pp. 505-509.
Huo et al., "Circulating activated platelets exacerbate atherosclerosis in mice deficient in apolipoprotein E", Nat Med, 2003, 9(1), pp. 61-67.
Huo et al., "Myeloid Bmal1 deletion increases monocyte recruitment and worsens atherosclerosis", FASEB J, 2017, 31(3), pp. 1097-1106.
Ingle et al., "Cardiomyocyte-specific Bmal1 deletion in mice triggers diastolic dysfunction, extracellular matrix response, and impaired resolution of inflammation", Am J Physiol Heart Circ Physiol, 2015, 309(11), pp. H1827-H1836.
Kain et al., "Resolvin D1 activates the inflammation resolving response at splenic and ventricular site following myocardial infarction leading to improved ventricular function", J Mol Cell Cardiol, 2015, 84, pp. 24-35.
Khambata et al., "Anti-inflammatory actions of inorganic nitrate stabilize the atherosclerotic plaque", Proc Natt Acad Sci USA, 2017, 114(4), pp. E550-E559.
Markworth et al., "Divergent shifts in lipid mediator profile following supplementation with n-3 docosapentaenoic acid and eicosapentaenoic acid", FASEB J, 2016, 30(11), pp. 3714-3725.
McAlpine et al., "Circadian Influence on Metabolism and Inflammation in Atherosclerosis", Circ Res, 2016, 119(1), pp. 131-141.
Morin et al., "Anti-proliferative effects of a new docosapentaenoic acid monoacylglyceride in colorectal carcinoma cells", Prostaglandins Leukot Essent Fat Acids, 2013, 89, pp. 203-213.
Morin et al., "Docosapentaenoic acid monoacylglyceride reduces inflammation and vascular remodelling in experimental pulmonary hypertension" Am J Physiol Heart Circ Physiol, 2014, 307, pp. H574-H586.
Morin et al., "Eicosapentaenoic acid and docosapentaenoic acid monoglycerides are more potent than docosahexaenoic acid monoglyceride to resolve inflammation in a rheumatoid arthritis model", Arthritis Res Ther, 2015, 17(142), pp. 1-12.
Muller et al., "Circadian variation in the frequency of onset of acute myocardial infarction", N Engl J Med, 1985, 313 (21), pp. 1315-1322.
Murphy et al., "Diets enriched in menhaden fish oil, seal oil, or shark liver oil have distinct effects on the lipid and fatty-acid composition of guinea pig heart", Mol Cell Biochem, 1997, 177, pp. 257-269.
Murphy et al., "Dietary menhaden, seal, and corn oils differentially affect lipid and ex vivo eicosanoid and thiobarbituric acid-reactive substances generation in the guinea pig", Lipids, 1999, 34, pp. 115-124.
Nakashima et al., "Impact of Morning Onset on the Incidence of Recurrent Acute Coronary Syndrome and Progression of Coronary Atherosclerosis in Acute Myocardial Infarction" Circ J, 2017, 81(3), pp. 361-367.
Norris et al., "A cluster of immunoresolvents links coagulation to innate host defense in human blood", Sci Signal, 2017, 10(490), pp. 1-11.
Pfluecke et al., "Monocyte-platelet aggregates and CD11b expression as markers for thrombogenicity in atrial fibrillation", Clin Res Cardiol, 2016, 105(4), pp. 314-322.
Puttonen et al., "Is shift work a risk factor for rheumatoid arthritis? The Finnish Public Sector study", Ann Rheum Dis, 2010, 69(4), pp. 779-780.
Ramakrishnan et al., "Platelet activating factor: A potential biomarker in acute coronary syndrome?", Cardiovasc Ther, 2017, 35(1), pp. 64-70.
Sakata et al., "Circadian fluctuations of tissue plasminogen activator antigen and plasminogen activator inhibitor-1 antigens in vasospastic angina", Am Heart J, 1992, 124(4), pp. 854-860.
Samuelsson, "Role of basic science in the development of new medicines: examples from the eicosanoid field", J Biol Chem, 2012, 287(13), pp. 10070-10080.
Scheer et al., "The human endogenous circadian system causes greatest platelet activation during the biological morning independent of behaviors", PLoS One, 2011, 6(9), pp. e24549.
Serhan, "Treating inflammation and infection in the 21st century: new hints from decoding resolution mediators and mechanisms", FASEB J, 2017, 31, pp. 1273-1288.
Shea et al., "Existence of an endogenous circadian blood pressure rhythm in humans that peaks in the evening" Circ Res, 2011, 108(8), pp. 980-984.
Shinohara et al., "Cell-cell interactions and bronchoconstrictor eicosanoid reduction with inhaled carbon monoxide and resolvin D1", Am J Physiol Lung Cell Mol Physiol, 2014, 307(10), pp. L746-L757.

(56) References Cited

OTHER PUBLICATIONS

Tsuji et al., "Docosapentaenoic acid (22:5, n-3) suppressed tube-forming activity in endothelial cells induced by vascular endothelial growth factor", Prostaglandins Leukot Essent Fat Acids, 2003, 68, pp. 337-342.

Zhang et al., "Resolvin D2 Enhances Postischemic Revascularization While Resolving Inflammation", Circulation, 2016, 134(9), pp. 666-680.

* cited by examiner

METHOD AND APPARATUS FOR DETERMINING THE EFFICACY OF STATINS FOR TREATING INFLAMMATORY DISEASES IN INDIVIDUAL PATIENTS

FIELD OF THE INVENTION

The present invention relates to methods for determining the efficacy of statins for treating inflammatory diseases such, for example, as cardiovascular disease and rheumatoid arthritis in individual patients. The invention also provides computer software, apparatus, immunoassays and devices for performing the methods of the invention.

BACKGROUND TO THE INVENTION

Acute inflammation is host protective and mounts in response to tissue injury from within or invading microbes. It is now recognised that failure to engage resolution mechanisms could underlie persistent low-grade inflammation that is associated with many chronic diseases including rheumatoid arthritis, periodontal disease, asthma, diabetes and inflammatory bowel disease (IBD), as well as neurological disorders such as Alzheimer's disease.

It is now appreciated that resolution of self-limited inflammation is an active process regulated by local chemical mediators and their receptors. Families of specialised pro-resolving mediators (SPMs) termed resolvins, protectins and maresins have been discovered, each produced in self-limited inflammatory leukocyte-rich exudates. Their biosynthetic metabolomes are temporally regulated in the resolution phase of acute inflammation.

SPMs and their respective metabolomes exert potent leukocyte-directed actions, stimulating key signs of resolution, namely, limiting further polymorphonuclear leukocyte (PMN) recruitment (cessation as stop signals) to a site and enhance macrophage uptake of debris, bacteria and apoptotic cells. In addition, each individual SPM may evoke further characteristic properties within programmed resolution. For example, resolvin RvE1 rescues failed phagocytic activities of human macrophages from periodontitis patients; D-series resolvins (i.e., RvD1, RvD2, and RvD5) enhance bacterial containment by the host, thus lowering the dose of antibiotics needed to kill and clear bacteria. Meanwhile, Maresin 1 (MaR1), from the maresin (MaR) pathway, stimulates resolution as well as tissue regeneration, and protectins improve influenza infection by directly inhibiting viral replication in mice.

These resolution phase SPMs and their metabolomes include resolvins, protectins and maresins as well as lipoxins. These mediators counter-regulate the actions of the classic proinflammatory initiators, prostaglandins (PGs) and leukotrienes (LTs).

The structures of these lipid mediators have been found to be conserved throughout evolution, including tunicates, mice and baboons as well as humans, facilitating the direct translation of findings made in experimental systems to humans and vice versa.

Dalli J, Chiang N and Serhan C N. Elucidation of novel 13-series resolvins derived from n-3 docosapentaenoic acid (n-3 DPA) that increase with atorvastatin and clear infections. *Nature Medicine.* 2015; 21:1071-1075 and WO 2017/015271 A1 disclose structures of four new host-protective molecules, termed 13-series resolvins (RvTs), that are produced in neutrophil-endothelial co-cultures and present in human and mouse tissues after sterile inflammation or infection. Their biosynthesis during neutrophil-endothelial cell interactions was initiated by endothelial cyclooxygenase-2 (COX-2), increased by atorvastatin via S-nitrosylation of COX-2 and reduced by COX-2 inhibitors. The actions of atorvastatin and RvTs were additive in *E. coli* infections in mice, where they accelerated resolution of inflammation and increased survival>60%. These molecules regulate key innate protective responses in the resolution of infectious inflammation.

Rheumatoid arthritis is characterised by an unabated inflammatory response that progressively leads to joint destruction and can ultimately be debilitating. This persistent inflammatory response is also thought to be an underlying cause for the increased risk of developing cardiovascular disease (CVD) in patients with arthritis. In this context, statins protect from CVD, and recent studies suggest that they also reduce disease activity in patients with rheumatoid arthritis.

Statins are a class of lipid-lowering medications and, at the time of writing, are amongst the most widely used medications in the Western world. The percentage of adults 45 years of age and over using statin drugs has increased from 2.4% from 1988 to 1994 to 25.1% from 2005 to 2008.

Statins have been found to reduce CVD and mortality in those who are at high risk.

WO 02/24194 A2 discloses a method to achieve MHC-class II mediated immunomodulation in a mammal in need of such treatment, which comprises administering to the mammal at least one statin, or a functionally or structurally equivalent molecule, in an amount effective to modulate MHC class II expression in the mammal. The mammal may be suffering from an autoimmune disease selected from type I diabetes, multiple sclerosis, rheumatoid arthritis, Crohn's disease or lupus erythematosus.

Statins are HMG-CoA reductase inhibitors, but it is evident that these pleiotropic actions of statins cannot be uniquely ascribed to inhibition of HMG-CoA reductase activity.

Despite effective low density-lipoprotein cholesterol (LDL-C) reduction with statins, a large amount of residual risk remains in patients treated with statins. For example, in randomised placebo controlled trials a mean 27% relative risk reduction equates to a 3.4% absolute risk reduction. One possible explanation for the large residual risk following statin therapy may be the heterogeneity of statin responsiveness within the human population. Patients may differ in three ways: (1) the effect of statins on lipoprotein metabolism and, primarily, LDL-C reduction; (2) the response to statin therapy in terms of clinical event benefit, which may be independent of the lipoprotein response; and (3) the adverse effects attributed to statin use. Blood lipid levels are expected to be modulated by genetic variants that alter the function and activity of the molecules in lipid and cholesterol pathways. These genetic variants and others that affect statin pharmacokinetics may also affect statin responsiveness (Superko H R, Momary K M, Li Y, et al. Statins Personalized. *Med. Clinics of N. Am.* 2012; 96(1):123-139).

Studies investigating potential mechanisms that may be engaged by statins found that atorvastatin and lovastatin upregulate the formation of the pro-resolving mediator 15-epi-LXA$_4$ that mediates their protective actions in cardiovascular and mucosal protection respectively (Birnbaum Y, Ye Y, Lin Y, et al. Augmentation of myocardial production of 15-epilipoxin-a4 by pioglitazone and atorvastatin in the rat. *Circulation.* 2006; 114(9):929-935. Planaguma A, Pfeffer M A, Rubin G, et al. Lovastatin decreases acute mucosal inflammation via 15-epi-lipoxin A4. *Mucosal Immunol.* 2010; 3(3):270-279).

There is a need for ascertaining which statins are more likely to be effective for treating different patients with CVD, rheumatoid arthritis or other inflammatory conditions, to provide a degree of personalisation of treatment with statins to individual patients.

It is an object of the present invention therefore to provide a method for assessing whether a given statin is likely to be effective for use in treating an inflammatory condition in an individual patient.

SUMMARY OF THE INVENTION

In accordance with a first aspect of the present invention therefore there is provided method of assessing the efficacy of a statin for use in the treatment of an inflammatory condition in an individual patient, which comprises measuring the levels of at least one 13-series resolvin in biological samples obtained from the patient before and after administration of the statin, wherein an increase in the level of the resolvin after administration of the statin is indicative of efficacy of the statin.

As described in the Examples below, the inventors have discovered that administration of two clinically relevant statins, atorvastatin or pravastatin, to mice during inflammatory arthritis (IA) upregulated systemic and tissue amounts of 13-series resolvins and significantly reduce joint disease. Meanwhile, administration of simvastatin did not significantly upregulate RvT and reduce joint inflammation. It was also found that atorvastatin and pravastatin each reduced systemic leukocyte activation including platelet-monocyte aggregates (~25-60%). These statins decreased neutrophil trafficking to the joint as well as joint monocyte macrophage numbers. Atorvastatin and pravastatin gave significant reductions (~30-50%) in the expression of CD11b and major histocompatibility complex class II (MHCII) on both monocyte and monocyte-derived macrophages in the joints. Administration of an inhibitor to cyclo-oxygenase (COX)-2, the initiating enzyme in the RvT pathway, reversed the protective actions of these statins on both joint and systemic inflammation.

Together these findings indicate that the 13-series resolvins may be useful in measuring the anti-inflammatory actions of statins.

In some embodiments, the at least one 13-series resolvin may be selected from RvT1 (7,13,20-trihydroxy-8,10,14,16Z,18-docosapentaenoic acid), RvT2 (7,12,13-trihydroxy-8,10,14,16Z,19Z-docosapentaenoic acid), RvT3 (7,8,13-trihydroxy-9,11,14,16Z,19Z-docosapentaenoic acid) and RvT4 (7,13-dihydroxy-8,10,14,16Z,19Z-docosapentaenoic acid).

In some embodiments, the levels of two or more of the 13-series resolvins in the biological samples may be measured.

In some embodiments, the levels of three or all four of the 13-series resolvins in the biological samples may be measured.

The structures of the 13-series resolvins, which are derived from n-3 DPA and are called "13-series" owing to the hydroxyl group at the C13 position, are as follows:

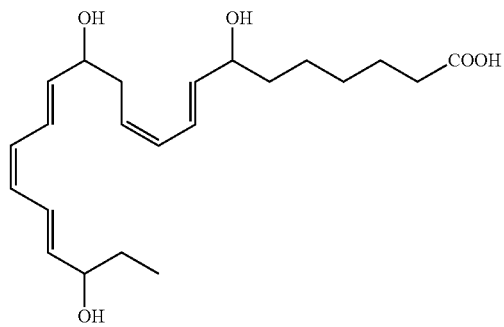

(8E,10Z,14E,16Z,18E)-7,13,20-trihydroxy-8,10,14,16,18-docosapentaenoic acid

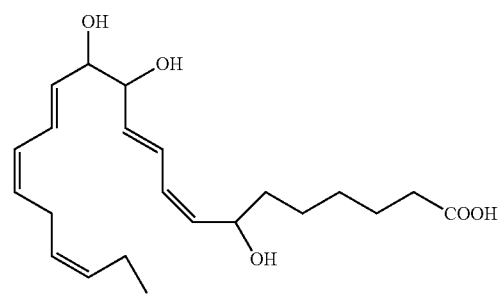

(8Z,10E,14E,16Z,19Z)-7,12,13-trihydroxy-8,10,14,16,19-docosapentaenoic acid

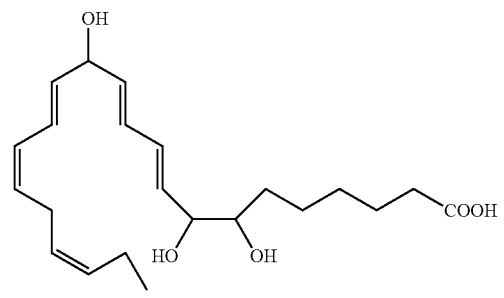

(9E,11E,14E,16Z,19Z)-7,8,13-trihydroxy-9,11,14,16,19-docosapentaenoic acid

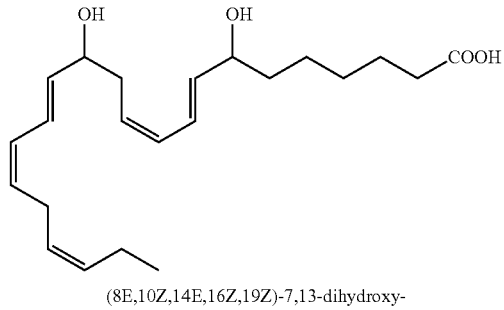

(8E,10Z,14E,16Z,19Z)-7,13-dihydroxy-8,10,14,16,19-docosapentaenoic acid

Conveniently, the samples may be blood, serum or plasma samples.

Suitably the samples may be treated immediately after collection with an anticoagulant such, for example, as heparin to prevent clotting.

If the samples—for example human serum samples—are required to be stored prior to analysis, they may be placed in an organic solvent and stored at a temperature of −75° C. or below, e.g., −80° C. Suitably, the organic solvent may comprise or consist of methanol. Although lipid mediators have been found to be unstable in frozen samples during the term-long-term storage, with the levels of some of the mediators being significantly (>50%) reduced following three-month storage, it has been surprisingly found that by using methanol, and optionally other organic solvents, the stability of these molecules may be improved when they are stored for an extended period at temperatures of −75° C. and below. More generally any $C_{1-3}$ organic alcohol, such for example as a substituted or unsubstituted, straight or branched chain $C_{1-3}$ alkanol, or a mixture or two or more such solvents may be used. Suitably, the samples may be stored at temperatures of about −80° C. or less. The samples may be stored for at least about 1 month, and in some embodiments at least about 3 months, up to about 9 months or longer.

Deuterium labelled standards of the kind described below may be added to the samples prior to freezing.

Methods for measuring the levels of 13-series resolvins in biological samples such as blood and tissue are available to those skilled in the art and need not be described herein in detail.

Suitable methods are disclosed, for example, in Yang R, Chiang N, Oh S F and Serhan C N. 2011. "Metabolomics-Lipidomics of Eicosanoids and Docosanoids Generated by Phagocytes". *Curr Protoc Immunol.* 95:14.26:14.26.1-14.26.26 and Dalli J and Serhan C N. 2012. "Specific lipid mediator signatures of human phagocytes: microparticles stimulate macrophage efferocytosis and pro-resolving mediators". *Blood.* 2012; 120:e60-e72, the contents of both of which are incorporated herein by reference.

Briefly, in some embodiments, the levels of the at least one 13-series resolvin in the samples may be measured using liquid chromatography tandem mass spectrometry (LC-MS/MS) after extracting the SPMs from the samples.

The SPMs may be extracted from the samples using solid-phase extraction, for instance using C18 columns. Suitable methods are disclosed by Colas R A, Shinohara M, Dalli J, Chiang N and Serhan C N. "Identification and signature profiles for pro-resolving and inflammatory lipid mediators in human tissue". *Am J Physiol Cell Physiol.* 2014; 307:C39-54, the contents of which are incorporated herein by reference.

One or more internal labelled standards may be added to the samples prior to extraction of the SPMs to facilitate quantitation of the 13-series resolvin in the samples. Suitable labelled standards are deuterium-labelled 5S-HETE (5S-HETE-$d_8$), deuterium-labelled leukotriene $B_4$ (LTB$_4$-$d_4$), deuterium-labelled lipoxin $A_4$ (LXA$_4$-$d_5$), deuterium-labelled resolvin D2 (RvD2-$d_5$) and deuterium-labelled prostaglandin $E_2$ (PGE$_2$-$d_4$).

The identity of a 13-series resolvin in a sample may be confirmed by matching its retention time (RT) and at least 6 diagnostic ions from its MS-MS spectrum with those of a synthetic or authentic standard for the SPM. Retention times for molecules measured using liquid chromatography are often instrument specific, but in some embodiments, the retention times of the above-mentioned 13-series resolvins may be as shown in Table 1 below:

TABLE 1

| 13-series resolvin (RvT) | Retention time ($R_T$) |
|---|---|
| RvT1 | 10.8 min ± 0.3 min |
| RvT2 | 11.2 min ± 0.3 min |
| RvT3 | 11.5 min ± 0.3 min |
| RvT4 | 13.6 min ± 0.3 min |

Quantitation may be achieved using linear regression curves that are constructed using a synthetic or authentic standard for the mediator.

LC-MS/MS may be suitable for use in situations where there is access to the equipment required such, for example, in hospital laboratories. However, more conveniently, the levels of the at least one 13-series resolvin in the samples may be measured using an immunoassay. Immunoassays have the potential to be miniaturised to run on a microfluidics device or test-strip and may be more suited for clinical point-of-care applications. Embodiments of the invention which incorporate an immunoassay may therefore be used in situ by a primary healthcare provider for assistance in prescribing a statin for an individual patient.

The levels of the at least one 13-series resolvin may be measured using a homogeneous or heterogeneous immunoassay.

Thus, in some embodiments, the levels of the or each 13-series resolvin may be measured in solution by binding to labelled antibodies that are present in excess, whereby binding alters detectable properties of the label. The amount of a specific SPM present will therefore affect the amount of the label with a particular detectable property. As is well known in the art, the label may comprise a radioactive label, a fluorescent label or an enzyme having a chromogenic or chemiluminescent substrate that is coloured or caused or allowed to fluoresce when acted on by the enzyme.

The antibodies may be polyclonal or monoclonal with specificity for the 13-series resolvin. In some embodiments, monoclonal antibodies may be used.

Alternatively, a heterogeneous format may be used in which the at least one 13-series resolvin is captured by surface-bound antibodies for separation and quantification. In some embodiments, a sandwich assay may be used in which a surface-bound 13-series resolvin is quantified by binding a labelled secondary antibody.

Suitably, the immunoassay may comprise an enzyme immunoassay (EIA) in which the label is an enzyme such, for example, as horseradish peroxidase (HRP). Suitable substrates for HRP are well known in the art and include, for example, ABTS, OPD, AmplexRed, DAB, AEC, TMB, homovanillic acid and luminol. In some embodiments, an ELISA immunoassay may be used; a sandwich ELISA assay may be particularly preferred.

The immunoassay may be competitive or non-competitive. Thus, in some embodiments, the amounts of the at least one 13-series resolvin may be measured directly by a homogeneous or heterogeneous method, as described above. Alternatively, the 13-series resolvin in the samples may be sequestered in solution with a known amount of antibody which is present in excess, and the amount of antibody remaining then determined by binding to surface-bound SPM to give an indirect read-out of the amount of 13-series resolvin in the original sample. In another variant, the at least one 13-series resolvin may be caused to compete for binding to a surface bound antibody with a known amount of a labelled SPM.

The surface bound antibodies or SPM may be immobilised on any suitable surface of the kind known in the art. For instance, the antibodies or SPM may be immobilised on a surface of a well or plate or on the surface of a plurality of magnetic or non-magnetic beads.

In a second aspect of the present invention therefore there is provided an immunoassay for measuring the level of a 13-series resolvin in a biological sample, the immunoassay comprising antibodies to the 13-series resolvin that are coated on a surface for capturing the 13-series resolvin in the sample and/or tagged with a label that is altered in a detectable manner by binding to the 13-series resolvin in the sample, or an amount of the 13-series resolvin, which is the same as the one to be quantitated in the sample, that is immobilised on a surface for capturing antibodies to the 13-series resolvin after mixing with the sample.

In some embodiments, the immunoassay may be a competitive assay, further comprising a known amount of the 13-series resolvin, which is the same as the one to be quantitated in the sample, but tagged with a detectable label. The labelled 13-series resolvin may be affinity-bound to a suitable surface by an antibody to the 13-series resolvin. Upon adding the sample a proportion of the labelled 13-series resolvin may be displaced from the surface-bound antibodies, thereby providing a measure of the level of 13-series resolvin in the sample.

In some embodiments, the immunoassay may comprise surface-bound 13-series resolvin, which is the same as the 13-series resolvin that is to be quantitated in the sample, and a known amount of antibodies to the 13-series resolvin in solution in excess. The sample is first mixed with the antibodies in solution such that a proportion of the antibodies bind with the 13-series resolvin in the sample. The amount of unbound antibodies remaining can then be measured by binding to the surface-bound 13-series resolvin.

In some embodiments, the immunoassay may comprise a labelled secondary antibody to the 13-series resolvin or to a primary antibody to the 13-series resolvin for quantifying the amount of the 13-series resolvin bound to surface-bound antibodies or the amount of primary antibody bound to the 13-series resolvin immobilised on a surface.

In a third aspect of the present invention, there is provided equipment for measuring the level of a specific 13-series resolvin in a sample comprising a sample collection device and an immunoassay according to the second aspect of the invention.

Suitably the equipment may further comprise a detector for detecting labelled 13-series resolvin or labelled antibodies to the 13-series resolvin in the immunoassay. Suitable labels are mentioned above, but in a preferred embodiment, the label may be an enzyme having a chromogenic or chemiluminescent substrate that is coloured or caused or allowed to fluoresce when acted on by the enzyme.

In some embodiments, the immunoassay or equipment of the invention may be incorporated into a miniaturised device for measuring the level of at least one 13-series resolvin in a biological sample. Suitably, the device may comprise a lab-on-a-chip.

In accordance with a fourth aspect of the invention therefore, there is provided a device for measuring the level of at least one 13-series resolvin in a biological sample obtained from a patient, the device comprising one or more parts defining an internal channel having an inlet port and a reaction zone, in which a 13-series resolvin in a sample may be reacted with an immobilised primary antibody for the 13-series resolvin for capturing the 13-series resolvin, or a primary antibody for the 13-series resolvin in excess in solution after mixing with the sample upstream of the reaction zone may be reacted with 13-series resolvin, which is the same as the one to be measured in the sample, but immobilised on a surface within the reaction zone, for quantifying directly or indirectly the amount of the 13-series resolvin in the sample.

The captured 13-series resolvin or primary antibody may then be detected using a secondary antibody to the 13-series resolvin or primary antibody, which is tagged with an enzyme.

As described above, the enzyme may have a chromogenic or chemiluminescent substrate that is coloured or caused or allowed to fluoresce when acted on by the enzyme. Suitably, the one or more parts of the device defining the channel, at least adjacent the reaction zone, may be transparent to light, at least in a range of wavelengths encompassing the colour or fluorescence of the substrate to allow detection of a reaction between the 13-series resolvin or primary antibody and the secondary antibody using a suitable detector such, for example, as a photodiode, positioned outside the channel or further channel.

In some embodiments, the device may comprise a plurality of channels, each with its own inlet port, for measuring the levels of a plurality of different 13-series resolvins in the sample in parallel. Therefore, each channel may include a different respective immobilised primary antibody or 13-series resolvin.

Suitably, the device may comprise one or more selectively operable valves associated with the one or more inlet ports for controlling the admission of a sequence of different reagents into to the channels such, for example, as the sample, wash solutions, primary antibody, secondary antibody and enzyme substrate.

The device therefore may comprise a microfluidics device. The channel may include a reaction zone. Microfluidics devices are known to those skilled in the art. A review of microfluidic immunoassays or protein diagnostic chip microarrays is provided by Chin et al. 2012. *Lab on a Chip.* 2012; 12:2118-2134. A microfluidics device suitable for carrying out an ELISA immunoassay at a point-of-care is disclosed by Chan C D, Laksanasopin T, Cheung Y K, Steinmiller D et al. "Microfluidics-based diagnostics of infectious diseases in the developing world". *Nature Medicine.* 2011; 17(8):1015-1019, the contents of which are incorporated herein by reference.

In some embodiments, the statin may be selected from atorvastatin, cerivastatin, fluvastatin, lovastatin, mevastatin, pitavastatin, pravastatin, rosuvastatin and simvastatin.

Suitably, the statin may be administered to the patient in its normal initial or maintenance dose.

Accordingly, atorvastatin may be administered to the patient in a dose of about 5-80 mg, preferably 10-40 mg. Cerivastatin may be administered to the patient in a dose of about 0.2-0.8 mg. Fluvastatin may be administered to the patient in a dose of about 10-80 mg, preferably 20-80 mg. Lovastatin may be administered to the patient in a dose of about 5-60 mg, preferably 10-60 mg or 20-60 mg. Mevastatin may be administered to the patient in a dose of up to about 25 mg. Pitavastatin may be administered to the patient in a dose of about 0.5-4 mg, preferably about 1 mg or 2 mg. Pravastatin may be administered to the patient in a dose of about 20-80 mg, preferably 40-80 mg. Rosuvastatin may be administered to the patient in a dose of about 2.5-40 mg, preferably about 5-20 mg or 10-20 mg. Simvastatin may be administered to the patient in a dose of about 2.5-40 mg, preferably about 5-20 mg or 10-20 mg.

Suitably, the second sample may be taken at least 30 minutes after administration of the statin, preferably at least one hour, and more preferably at least two hours.

In some embodiments, the inflammatory condition may be cardiovascular disease (CVD).

In some embodiments, the inflammatory condition may be rheumatoid arthritis.

The present invention therefore provides a method of assessing the efficacy of a statin for use in the treatment of an inflammatory condition in an individual patient, which comprises comparing the levels of at least one 13-series resolvin in biological samples obtained from the patient before and after administration of the statin, wherein an increase in the level of the at least one resolvin after administration of the statin is indicative of efficacy of the statin.

The methods of the present invention may be performed by a computer.

In accordance with a fifth aspect of the invention therefore, there is provided a computer-implemented method of assessing the efficacy of a statin for use in the treatment of an inflammatory condition in an individual patient, which comprises receiving in a computer sample data representing the levels of at least one 13-series resolvin in biological samples obtained from the patient before and after administration of the statin and executing software on the computer to compare the levels of the at least one 13-series resolvin in the samples, an increase in the level of the at least one resolvin after administration of the statin being indicative of efficacy of the statin, and to output efficacy data representing the efficacy of the statin on the basis of the comparison.

In a sixth aspect, the invention provides a computer program comprising instructions which, when executed by a computer, cause the computer to carry out the method of the fifth aspect of the invention.

It will be appreciated that the step of comparing the levels of the at least one 13-series resolvin in the samples may be carried out on a different computer from a computer that initially receives data representing the levels of the 13-series resolvin in the samples.

In a seventh aspect of the invention, therefore, there is provided computer apparatus for assessing the efficacy of a statin for use in the treatment of an inflammatory condition in individual patient, which comprises a first device incorporating a computer, a second computer and a communication channel between the first device and second computer for the transmission of data therebetween; wherein the first device is arranged to receive sample data representing the levels of at least one 13-series resolvin in biological samples obtained from the patient before and after administration of the statin and to transmit the sample data to the second computer via the communication channel, and the second computer is arranged to execute software to compare the levels of the at least one 13-series resolvin in the samples to determine the efficacy of the statin for the individual patient, an increase in the level of the at least one 13-series resolvin after administration of the statin being indicative of efficacy, and output efficacy data representing the efficacy of the statin.

The second computer may be arranged to transmit the efficacy data to the first device via the communication channel, or to a third computer.

In some embodiments, the first device may incorporate an immunoassay, equipment or device according to the second, third or fourth aspects of the invention for measuring the level of at least one 13-series resolvin in a biological sample.

Following is a description by way of example only with reference to the accompanying drawings of embodiments of the present invention.

EXAMPLES

Example 1

Animals

Figure 1A:
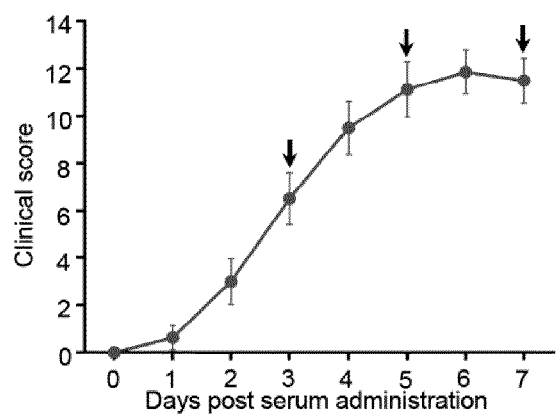
FIGS. 1A-1F: Increased RvT in paws from mice given atorvastatin and pravastatin during inflammatory arthritis. Arthritogenic K/BxN serum (100 µL, i.p.) was given to mice to initiate disease and (A) disease progression was monitored daily using clinical scores. Arrows denote days when mice were given statins or vehicle. (B-D) 0.2 mg/Kg atorvastatin, pravastatin, simvastatin or vehicle (DPBS containing 0.05% ethanol) were given i.v. on days 3, 5 and 7 after disease onset. Paws were collected on day 8 and lipid mediators were identified and quantified using lipid mediator profiling. (B) Representative MRM (multiple reaction monitoring) chromatograms of identified lipid mediators derived from docosahexaenoic acid, n-3 docosapentaenoic acid, eicosapentaenoic acid and arachidonic acid. (C) MS/MS spectra employed in the identification of RvT1, RvT2, RvT3 and RvT4. (D) Percent regulation of RvT1, RvT2, RvT3 and RvT4 compared to vehicle. (E) Representative MRM chromatograms of identified RvT. (F) Quantification of total RvT, RvT1, RvT2, RvT3 and RvT4 compared to vehicle. Results for A, B and E are representative of n=12 mice, for C and F are mean±s.e.m.; n=4 mice per group. * $p<0.05$ and ** $p<0.01$ vs. vehicle using one-way ANOVA with post hoc Dunnett's multiple comparisons test. Results are mean±s.e.m.; n=9 for vehicle, 11 for atorvastatin, 11 for pravastatin and 9 for simvastatin treated mice from 4 independent experiments. * $p<0.05$ vs. vehicle.

Male C57BL/6 mice (11 weeks old) were procured from Charles River (Kent, UK). All animals were provided with standard laboratory diet and water ad libitum and kept on a 12 h light/dark cycle.

Inflammatory Arthritis

The mice were administered K/BxN serum (100 µL, i.p.) on days 0 and 2 to initiate inflammatory arthritis. The mice were then given atorvastatin, pravastatin, simvastatin (0.2 mg/Kg each) or vehicle (DPBS−/− containing 0.05% ethanol) via i.v. injection on days 3, 5 and 7. Clinical scores were monitored daily using a 26-point arthritic scoring system. Swelling and redness of ankles/wrists, pads and digits of mice were inspected daily as described in Norling L V, Headland S E, Dalli J, et al. "Proresolving and cartilage-protective actions of resolvin D1 in inflammatory arthritis". *JCI Insight*. 2016; 1(5):e85922. Blood and paws were collected at the indicated time intervals.

In select experiments, mice were given 10 mg/Kg celecoxib 1 hour prior to statin injections. Blood and paws were collected either on day 8 after arthritis onset or 2 h after statin injection on day 7.

Lipid Mediator Profiling

Ice-cold methanol containing 500 pg of each deuterated (d) internal standard: $d_8$-SSHydroxyeicosatetraenoic, $d_4$-Leukotriene (LT) $B_4$, $d_5$-Lipoxin (LX) $A_4$, d-Prostaglandin (PG) $E_2$ and $d_5$-Resolvin $D_2$, was added to samples. Lipid mediators were extracted and profiling conducted as described in Dalli J et al. 2015 (ibid), Colas R A et al. 2014 (ibid) and Rathod K S, Kapil V, Velmurugan S, et al. "Accelerated resolution of inflammation underlies sex differences in inflammatory responses in humans". *J Clin Invest*. 2017; 127(1):169-182.

Flow Cytometry

Whole blood was collected using heparin-lined syringes via cardiac puncture. Cells were incubated with Fc-blocking IgG and fluorescent-labelled antibodies for 45 minutes on ice. Cells were washed and incubated with 0.1% Live/Dead stain for 30 minutes on ice. Red blood cells were lysed and fixed using Whole Blood Lysing Reagent Kit. Staining was then evaluated using a flow cytometry analyser and analysed using suitable software.

Paws were harvested and leukocytes isolated as described in Dalli J et al. 2015 (ibid). Briefly, paws were incubated in RPMI-1640 (containing 0.5 µg/mL collagenase D and 40 g/mL DNAse I) at 37° C. for 30 minutes with vigorous agitation. Isolated cells were passed through a 70 µM strainer and suspended in RPMI-1640 containing 2 U/mL penicillin, 100 mg/mL streptomycin and 10% FBS, then centrifugated at 400×g, 10 minutes. Isolated cells were suspended in DPBS−/− containing 0.02% BSA and 1% Fc-blocking IgG (v/v), and incubated with 0.1% Live/Dead stain for 20 minutes on ice. Cells were washed using DPBS−/− and incubated with fluorescent-labelled antibodies for 45 minutes on ice. These were then washed and fixed using 1% paraformaldehyde. Absolute counting beads were used for leukocyte enumeration. Staining was then evaluated using a flow cytometry analyser and analysed using suitable software.

Human Neutrophil—Endothelial Cell Isolation

Umbilical cords were collected by the midwifery staff of the Maternity Unit, Royal London Hospital (protocol approved by East London and The City Health Authority Research Ethics Committee Number: 06/Q0605/40) and human umbilical vein endothelial cells were isolated as described in Gittens B R, Wright R D, Cooper D. Methods for assessing the effects of galectins on leukocyte trafficking. *Methods Mol Biol.* 2015; 1207:133-151. Cells were then incubated with Interleukin (IL)-1β and Tumour Necrosis Factor (TNF)-α (10 ng/mL each, 16 h, 37° C., 5% $CO_2$).

Neutrophils were isolated from blood of healthy consenting donors in accordance with the Declaration of Helsinki and Queen Mary Research Ethics Committee approved protocol (QMREC 2014:61). Incubations were conducted as described in Dalli J et al. 2015 (ibid).

Statistics

Results are presented as mean±s.e.m. Differences between groups were tested using GraphPad Prism 7 (GraphPad Software) and using one-way ANOVA with post hoc Dunnett's, Sidak's or Tukey's multiple comparisons test. Where appropriate one-sample t-test compared to normalized vehicle or two-way ANOVA were used. The criterion for statistical significance was $p<0.05$.

Results

Differential Regulation of Local and Systemic RvT by Atorvastatin, Pravastatin and Simvastatin During Inflammatory Arthritis It was first investigated whether atorvastatin regulated RvT formation during inflammatory arthritis and whether this action was unique to this statin or was shared with other clinically relevant statins, namely pravastatin and simvastatin. To test this, arthritogenic serum from K/BxN mice was administered on days 0 and 2. This serum leads to a Fcγ mediated immune response with a rapid onset and severe inflammatory arthritis.

Mice were then given atorvastatin (0.2 mg/Kg), pravastatin (0.2 mg/Kg) simvastatin (0.2 mg/Kg) or vehicle in a therapeutic paradigm on days 3, 5 and 7-post serum administration, at a time where clinical signs of disease were observed (FIG. 1A).

Figure 1B:
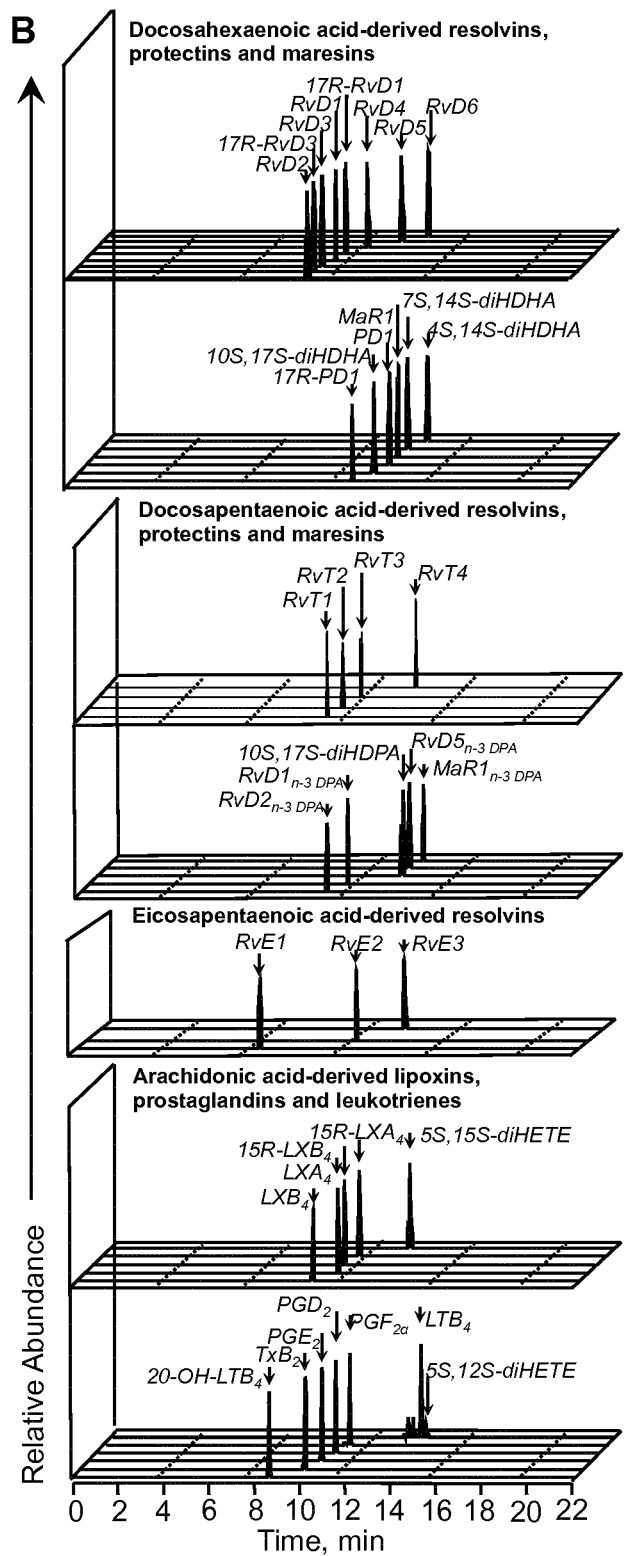
Figure 1C:
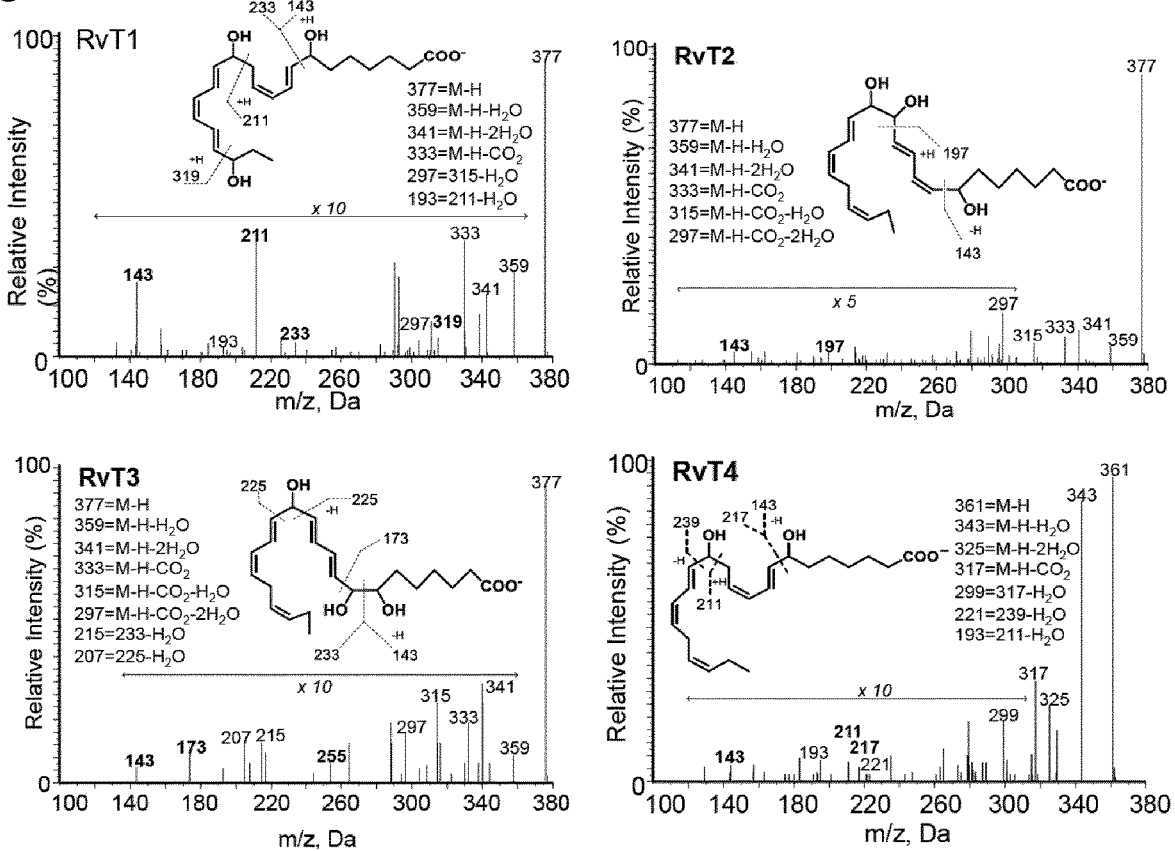

Plasma and paws were collected 24 h after the last statin dose, and lipid mediators were identified and quantified using liquid chromatography-tandem mass spectrometry (LC-MS/MS)-based lipid mediator profiling. In paws from arthritic mice mediators from all four major bioactive metabolomes were identified, including D-series resolvins and RvT (FIG. 1B, C). These mediators were identified in accordance with published criteria including matching retention times to authentic or synthetic standards (FIG. 1B) and at least 6 ions in the MS-MS as described in Colas R A et al. 2014 (ibid) (FIG. 1C).

Figure 1D:
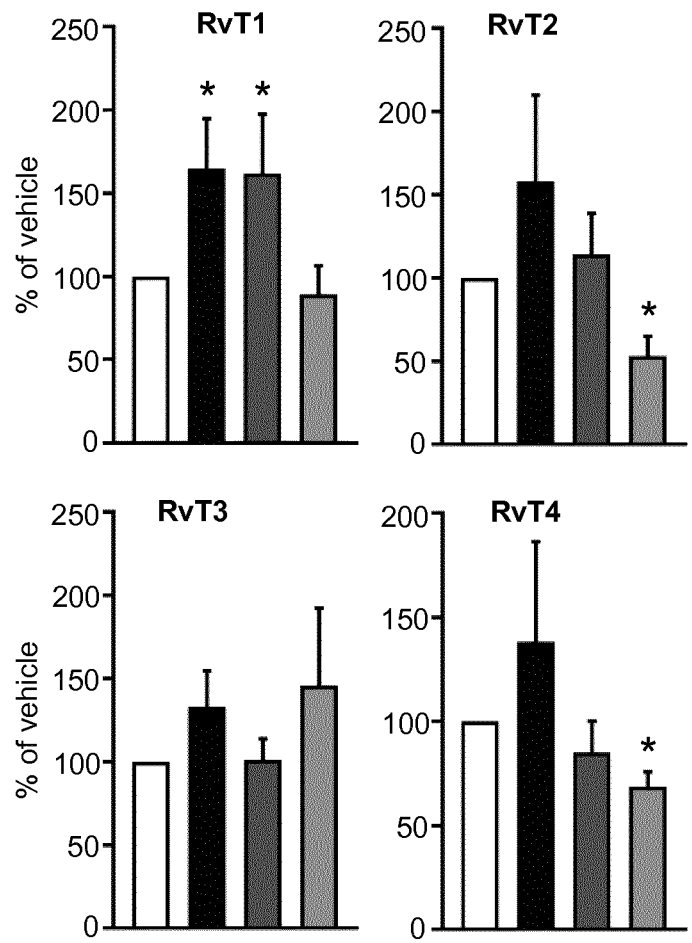

Using multiple reaction monitoring the concentrations of mediators identified in these paws were quantified. Here it was found that in joints from mice receiving atorvastatin there was a 43% increase in overall RvT amounts that was due to increased RvT1, RvT2, RvT3 and RvT4 when compared with paws from vehicle treated mice (FIG. 1D). Of note, the concentrations of these mediators were within their described bioactive ranges as reported in Dalli J et al. 2015.

Pravastatin also increased paw RvT by ~20% with increases in joint RvT1 and RvT2 concentrations, whereas simvastatin did not significantly increase joint RvT concentrations (FIG. 1D).

Assessment of plasma mediator levels demonstrated decreases in $LTB_4$, $PGD_2$, $PGE_2$, $PGF_{2\alpha}$ and $TxB_2$ in mice given either pravastatin or atorvastatin. In these mice, an increase in plasma levels of RvT concentrations were also found, with RvT1 being increased by both atorvastatin and pravastatin whereas RvT4 was only increased by atorvastatin.

Given that statins are rapidly cleared from the circulation, with a half-life for atorvastatin of ~14 h and pravastatin of ~3 h, it was next investigated whether systemic regulation of RvT biosynthesis by these statins was more pronounced immediately after dosing. For this purpose, arthritis was initiated using K/BxN serum and mice were given atorvastatin and pravastatin as described above. Blood was then collected 2 h after the last statin dose on day 7 and lipid mediators were identified and quantified using LM profiling.

Figure 1E:
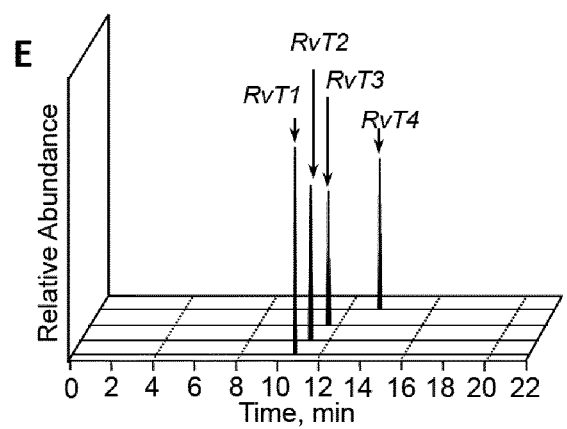
Figure 1F:
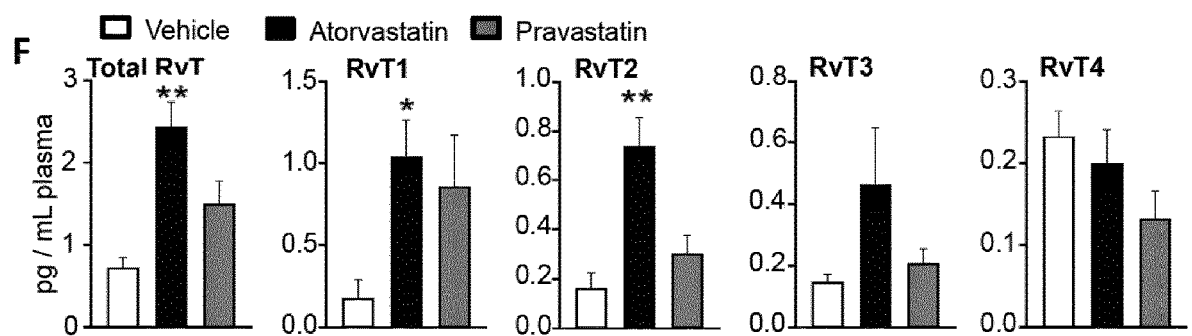

In plasma from mice given atorvastatin a significant increase (>200%) in RvT was found, with increases in RvT1, RvT2 and RvT3 when compared to vehicle treated mice (FIGS. 1E and 1F). In these mice, decreased circulating amounts of inflammation-initiating eicosanoids were found, including $PGD_2$ and $PGE_2$. Assessment of plasma LM profiles from mice given pravastatin also demonstrated a marked increase (>100%) in peripheral blood RvT with RvT1 demonstrating the highest increase when compared with vehicle treated mice (FIGS. 1E and 1F). In these mice, decreases in circulating $PGD_2$ (~46%) and $PGE_2$ (~29%) were also observed.

Together these results demonstrate that atorvastatin and pravastatin increase both joint and plasma RvT and decrease systemic inflammation during inflammatory arthritis.

Given that in the vasculature RvT are produced during neutrophil endothelial interactions, it was next questioned whether the increased RvT observed in murine systems by pravastatin were also translatable to humans. For this human neutrophil-endothelial cell co-cultures with pravastatin were incubated and its ability to regulate RvT was assessed.

Figure 2A:
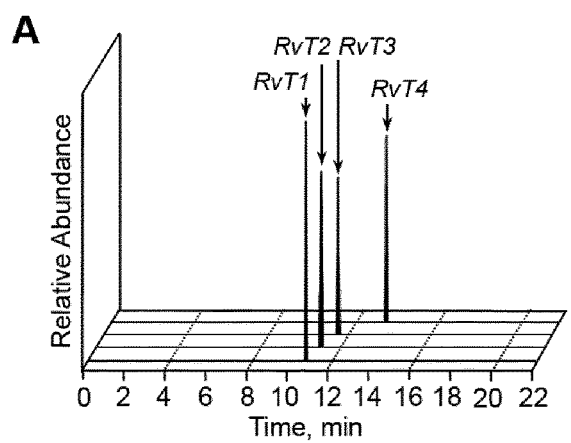
FIGS. 2A and 2B: Pravastatin dose-dependently increased RvT in human neutrophil-endothelial cell co-incubations. HUVEC ($8.5 \times 10^5$ cells/cm$^2$) were incubated with IL-1β (10 ng/mL) and TNF-α (10 ng/mL) for 16 h. These were then incubated with the indicated concentrations of atorvastatin, pravastatin or vehicle (DPBS containing 0.05% ethanol) for 30 minutes, then neutrophils ($4 \times 10^6$ cells/well) were added. Incubations were quenched after 1 h with 2 volumes of ice cold methanol and RvT were identified and quantified using lipid mediator profiling. (A) Representative MRM chromatograms of identified RvT. (B) RvT1, RvT2, RvT3 and RvT4 regulation compared with vehicle-treated incubations. Results are mean of 4 healthy donors from 4 independent experiments. *$p<0.05$ and **$p<0.01$ vs. vehicle using two-way ANOVA with post hoc Tukey's multiple comparisons test.
Figure 2B:
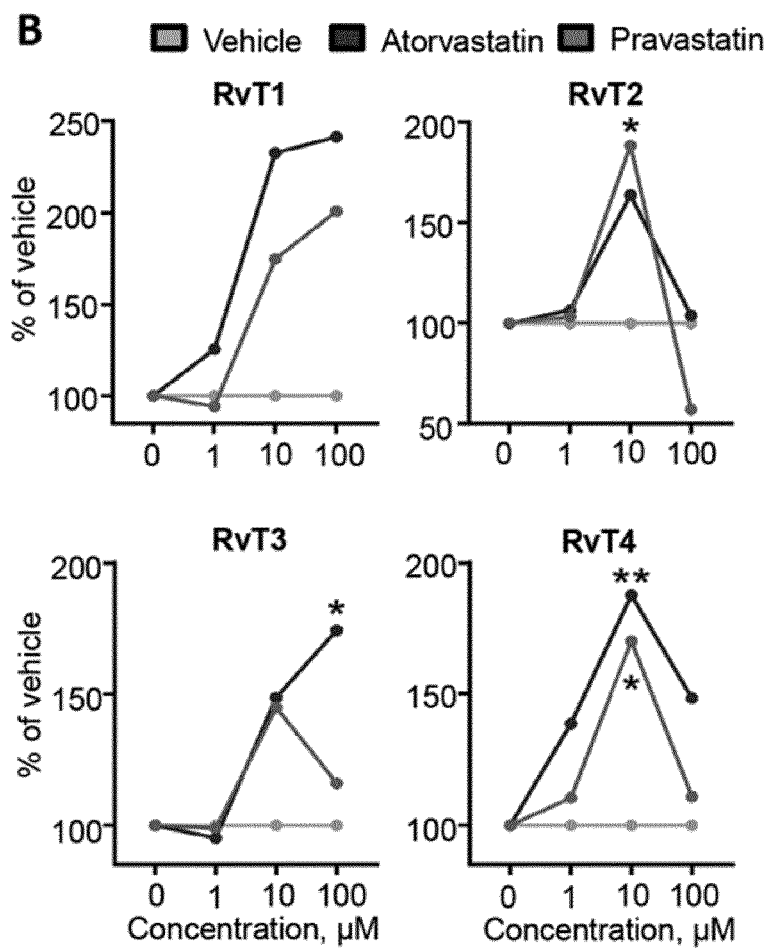

Here it was found that pravastatin dose-dependently upregulated the concentrations of all four RvT to a similar extent as that observed by atorvastatin (FIGS. 2A and 2B). Atorvastatin and Pravastatin Reduce Joint Inflammation and Protect Against Leukocyte Mediated Tissue Damage It was next investigated whether atorvastatin and pravastatin at doses that increased RvT also reduced joint inflammation. Arthritis was initiated and mice were treated and disease progression monitored as described above. In mice given vehicle, signs of disease were observed as early as day 2, disease severity reached a maximum at day 6 with a score of 11.9±0.9 after which the disease activity plateaued to day 7 (FIG. 3A).

When mice were given atorvastatin disease progression was dampened as early as day 4 (1 day after treatment initiation), with disease scores reaching a maximum score of 9.1±1.2 at day at 5. This reduction in disease activity was sustained through to day 7 (FIG. 3A).

Figures 3A, 3B, 3C, 3D:
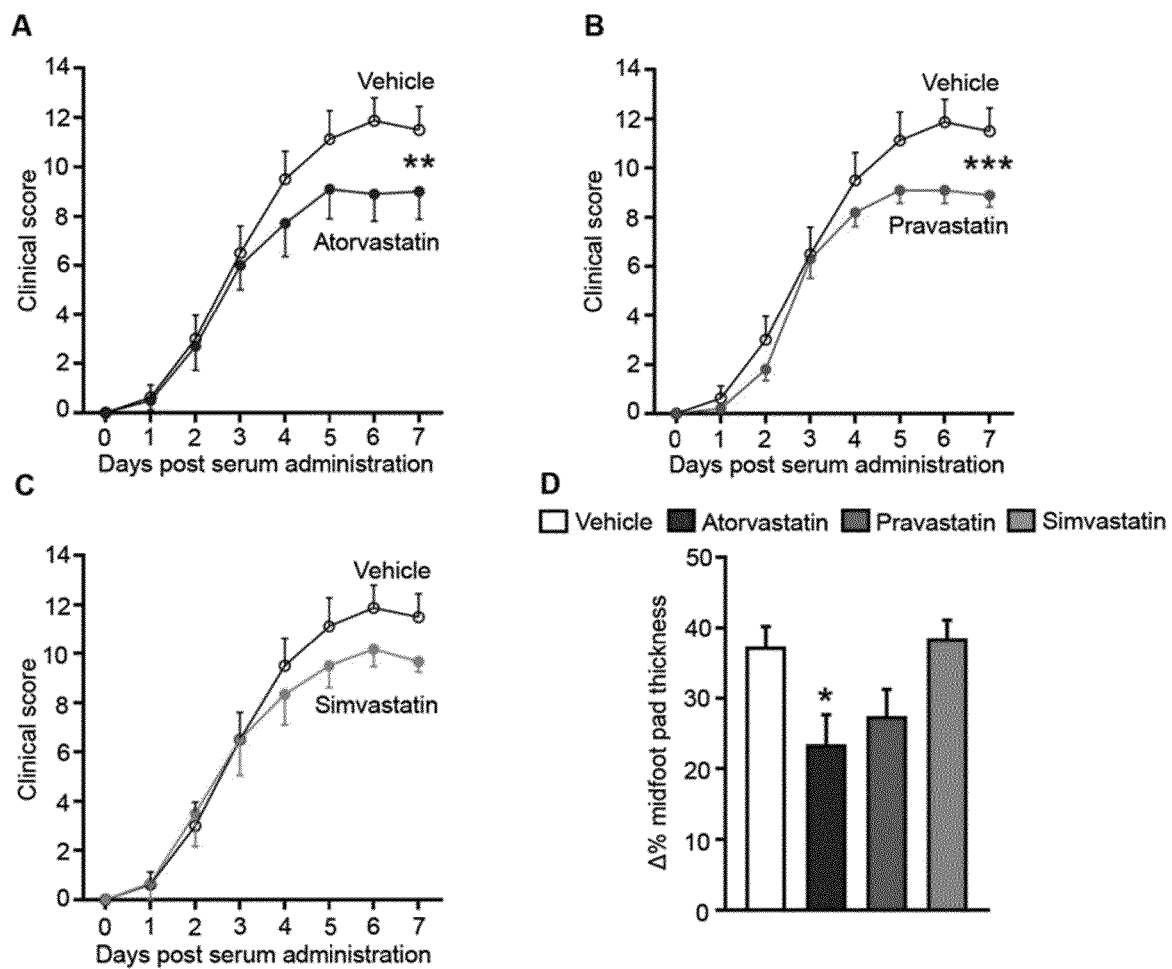
FIGS. 3A-3E: Atorvastatin and pravastatin reduced disease severity and protected joint architecture. Arthritogenic K/BxN serum was given to mice on days 0 and 2. Disease progression was monitored using a 26-point clinical score in mice given (A) atorvastatin (0.2 mg/Kg), (B) pravastatin (0.2 mg/Kg), (C) simvastatin (0.2 mg/Kg) or vehicle (DPBS containing 0.05% ethanol) on days 3, 5 and 7. Results are mean±s.e.m.; n=8 for vehicle, 10 for atorvastatin, 10 for pravastatin and 6 for simvastatin treated mice from 3 independent experiments.  $p<0.01$ and * $p<0.005$ vs. vehicle using ordinary two-way ANOVA (analysis of variance). (D) Maximum percentage increase in midfoot pad thickness. Results are mean±s.e.m.; n=8 for vehicle, 10 for atorvastatin, 10 for pravastatin and 6 for simvastatin treated mice from 3 independent experiments. * $p<0.05$ vs. vehicle using one-way ANOVA with post hoc Dunnett's multiple comparisons test. (E) Representative H&E-stained knee sections of mice (×4 magnification) collected on day 8 using EVOS FL imaging system. Results are representative of n=8 for vehicle, 10 for atorvastatin, 10 for pravastatin and 6 for simvastatin treated mice from 3 independent experiments. F, femur; T, tibia; m, meniscus; IFP, infrapatellar fat pad; PF, pannus formation. Arrows denote leukocyte infiltration.

Similarly, when mice were given pravastatin disease activity at day 5 was found to be lower when compared to mice given vehicle alone with a ~23% reduction in disease activity that was maintained through to day 7 (FIG. 3B).

Administration of simvastatin at equal doses to that of atorvastatin and pravastatin did not significantly reduce disease activity (FIG. 3C). These findings were also reflected in the extent of paw swelling where atorvastatin and pravastatin reduced joint swelling as measured by a decrease in midfoot pad thickness (FIG. 3D).

Figure 3E:
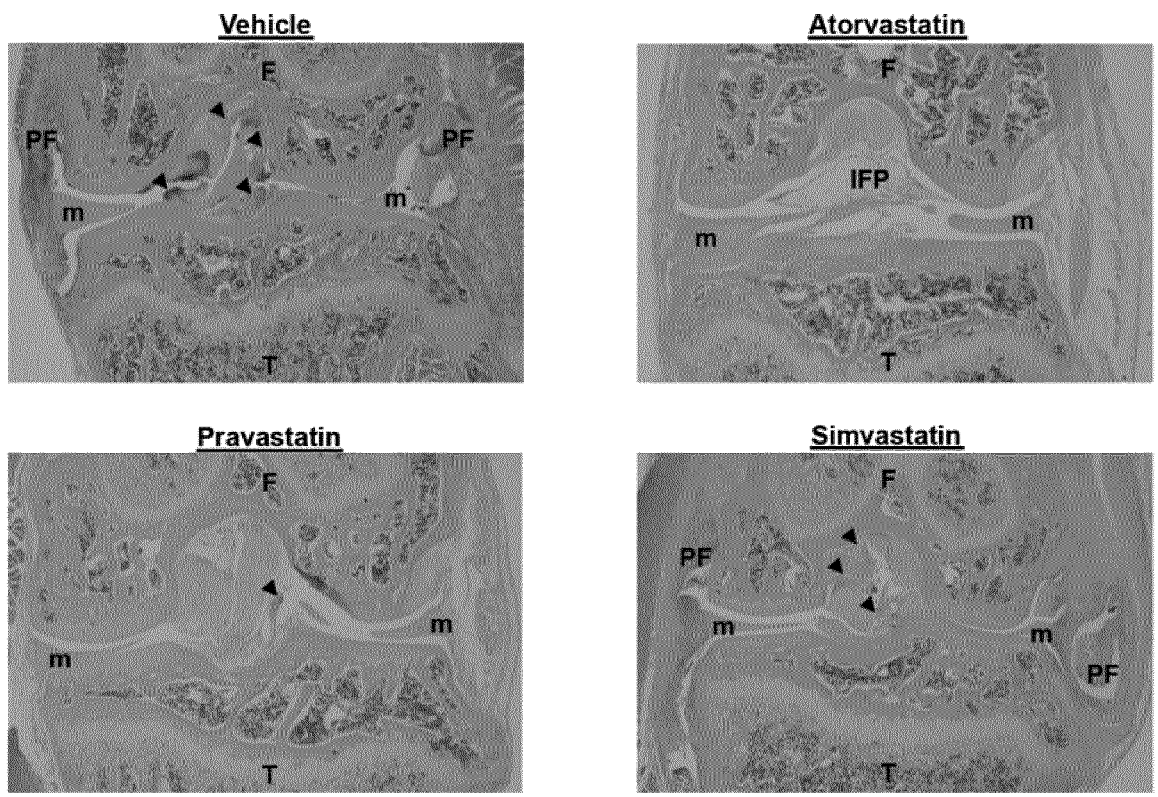

It was next assessed whether atorvastatin, pravastatin and simvastatin displayed joint protective actions. Haemotoxylin and eosin (H&E) stained sections of knee joints from mice given atorvastatin and pravastatin demonstrated reduced leukocyte infiltration, pannus formation and joint damage when compared with vehicle treated mice, whereas these parameters appeared to be unaltered in mice given simvastatin (FIG. 3E).

Together these findings demonstrate that atorvastatin and pravastatin are more potent than simvastatin at regulating local inflammation and protecting from leukocyte mediated joint damage in inflammatory arthritis.

Decreased Leukocyte Activation in Joints and Blood from Arthritic Mice by Atorvastatin and Pravastatin To ascertain whether these statins regulated systemic inflammation in inflammatory arthritis, the levels of platelet-leukocyte aggregates in peripheral blood from arthritic mice were assessed, given the relationship of these heterotypic aggregates and cellular activation with CVD.

Using flow cytometry it was found that atorvastatin regulated the expression of CD11b on both non-classical and classical monocytes as well as platelet-monocyte aggregates, measured by a decrease in CD62P (FIGS. 4A and B) and CD41 expression (n=9 mice) on these monocyte subsets.

Figures 4A, 4B, 4C, 4D:
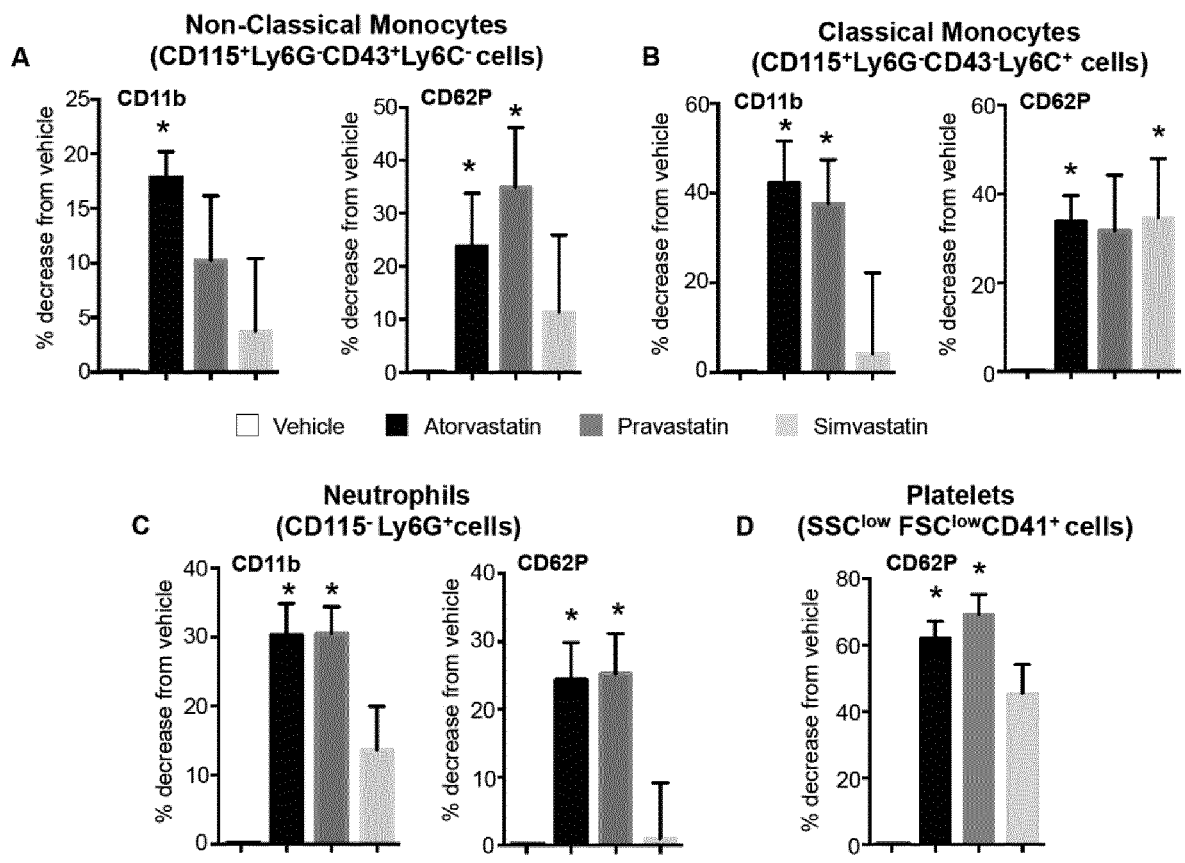
FIGS. 4A-4D: Differential regulation of circulating leukocyte and platelet activation by each of the statins in inflammatory arthritis. Serum-induced arthritis was initiated in mice and atorvastatin, pravastatin, simvastatin (0.2 mg/Kg each) or vehicle (DPBS containing 0.05% ethanol) were given on days 3, 5 and 7. On day 8 blood was collected. Leukocyte subsets and activation were identified using fluorescently labelled antibodies and flow cytometry. Activation markers on (A) non-classical monocytes, (B) classical monocytes, (C) neutrophils and (D) platelets were assessed as percentage decrease from vehicle. Results are mean±s.e.m.; n=9 for vehicle, 11 for atorvastatin, 11 for pravastatin and 9 for simvastatin treated mice from 4 independent experiments. * $p<0.05$ vs. vehicle using one-way ANOVA with post hoc Dunnett's multiple comparisons test.

Atorvastatin administration also regulated neutrophil and platelet responses, significantly reducing neutrophil CD11b expression, platelet-neutrophil aggregates (FIG. 4C) and decreasing platelet CD62P expression by ~60% (FIG. 4D), when compared with mice given vehicle alone. Similar findings were made with peripheral blood leukocytes and platelets from mice given pravastatin, where there was a reduction in monocyte CD11b expression (~10% for non-classical and ~40% for classical monocytes), platelet leukocyte aggregates (~35% for both monocyte subsets and ~25% for neutrophils) and platelet activation, with a reduction of ~70% in CD62P expression (FIG. 4). Simvastatin did not significantly regulate leukocyte CD11b expression, whereas heterotypic aggregates formed by classical monocytes and platelets and platelet CD62P expression were reduced (FIG. 4). These results demonstrate that atorvastatin and pravastatin regulate systemic inflammation dampening circulating monocyte, neutrophil and platelet activation during inflammatory arthritis.

It was next tested whether these actions also translated to a regulation of leukocyte trafficking and activation in the joint.

First, the trafficking of non-classical monocytes to the inflamed joints was assessed, given their role in disease onset and propagation of K/BxN serum initiated inflammatory arthritis.

Figures 5A, 5B, 5C:
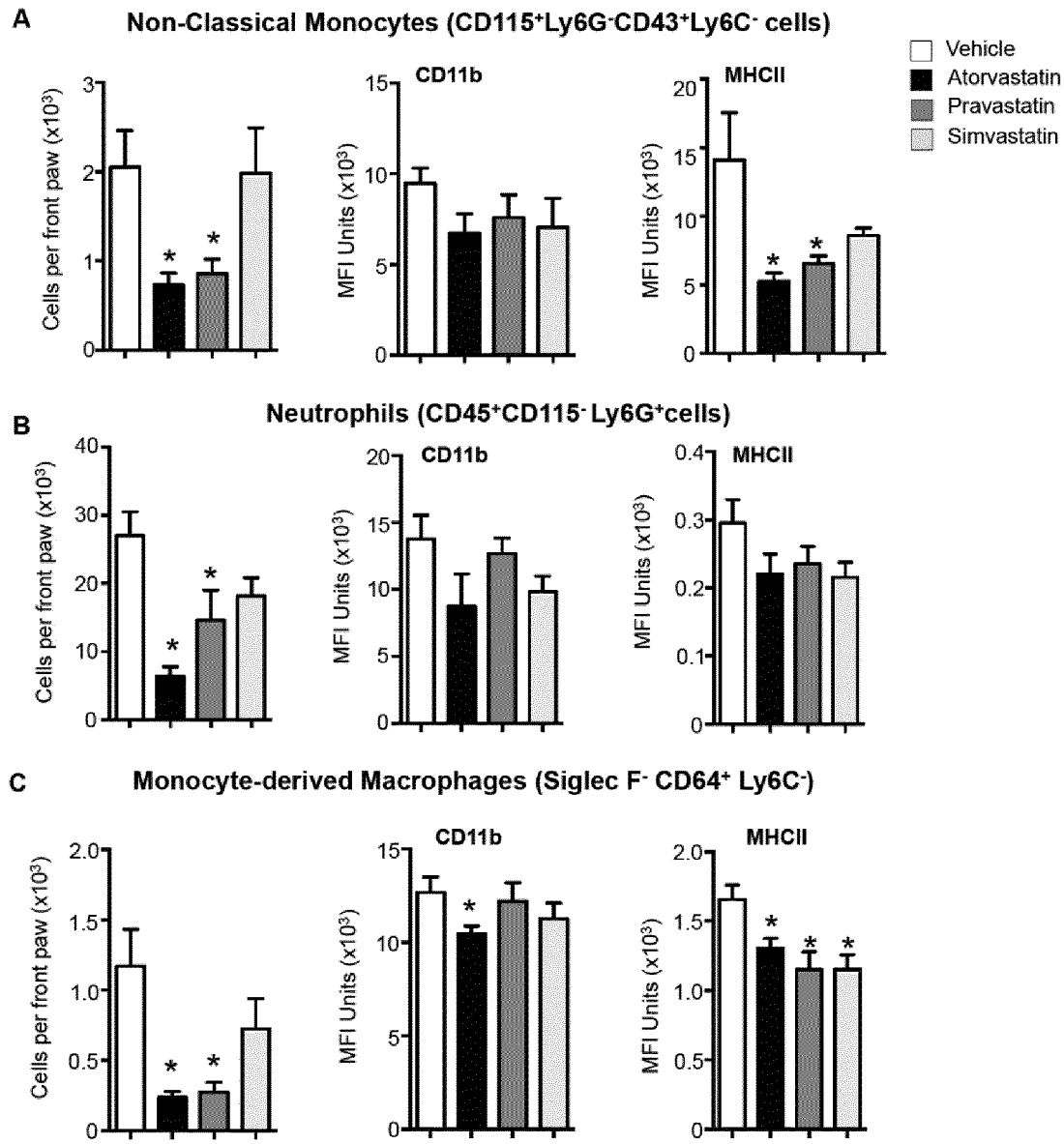
FIGS. 5A-5C: Reduction of monocyte, neutrophil and macrophage activation as well as trafficking to the joint by atorvastatin and pravastatin in inflammatory arthritis. Serum-induced arthritis was initiated in mice and atorvastatin, pravastatin, simvastatin (0.2 mg/Kg each) or vehicle (DPBS containing 0.05% ethanol) were given on days 3, 5 and 7. Front paws were collected on day 8 and digested to liberate infiltrating leukocytes. Leukocyte subsets were defined using antibodies against specific markers and flow cytometry. Trafficking and activation of (A) non-classical monocytes, (B) neutrophils, (C) monocyte-derived macrophages were assessed. Results are mean±s.e.m.; n=9 for vehicle, 11 for atorvastatin, 11 for pravastatin and 9 for simvastatin treated mice from 4 independent experiments. * $p<0.05$ vs. vehicle using one-way ANOVA with post hoc Dunnett's multiple comparisons test.

Flow cytometric analysis of leukocytes isolated from joints of mice given atorvastatin demonstrated a significant reduction in the total numbers of non-classical monocytes recruited to the joints (>60%). There also was a reduction in CD11b and a significant reduction in MHCII expression on these cells when compared to mice given vehicle alone (FIG. 5A). It was found that neutrophil trafficking was decreased in mice that received atorvastatin when compared to vehicle treated mice (FIG. 5B). In these mice, it was found that statin administration downregulated the expression of neutrophil CD11b and MHCII expression, although this did not reach statistical significance (FIG. 5B). Assessment of macrophage trafficking to the joints also demonstrated a significant reduction in the number of monocyte-derived macrophages as well as in the expression of activation markers CD11b and MHCII (FIG. 5C).

Similar findings were also made with mice given pravastatin that reduced joint monocyte, neutrophil and macrophage numbers as well as activation profile (FIG. 5).

Of note, although simvastatin regulated the expression of some of the activation markers on these cell subsets it did not significantly reduce leukocyte numbers in the paws when compared with mice given vehicle alone (FIG. 5).

Together these findings demonstrate that pravastatin and atorvastatin also regulate joint leukocyte trafficking and activation in inflammatory arthritis.

COX-2 Inhibition Reverses the Protective Actions of Atorvastatin and Pravastatin In order to assess the contribution of RvT in the protective actions exerted by atorvastatin and pravastatin, it was next investigated whether inhibition of COX-2, the initiating enzyme in the RvT pathway, reversed the protective actions of pravastatin and atorvastatin.

Figure 6A:
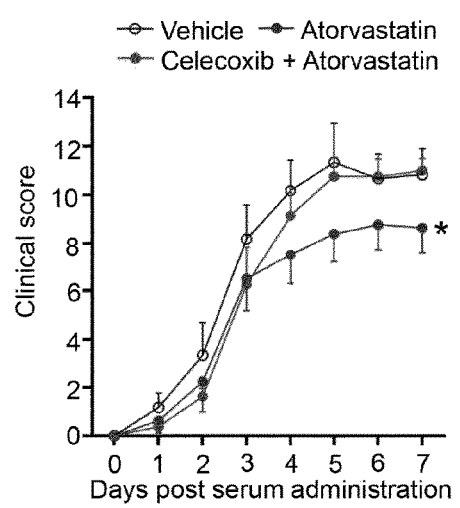
FIGS. 6A-6D: Inhibition of RvT production by celecoxib reverses the joint protective actions of atorvastatin and pravastatin. Inflammatory arthritis was initiated using arthritogenic serum (see methods for details). On days 3, 5 and 7 and mice were administered celecoxib (10 mg/Kg) or vehicle (DPBS containing 0.05% ethanol) and after 1 hour given (A) atorvastatin (0.2 mg/Kg), (B) pravastatin (0.2 mg/Kg) or vehicle (PBS containing 0.05% ethanol). Disease activity was assessed daily * $p<0.05$ vs. vehicle using ordinary two-way ANOVA. (C) On day 8 paws were collected and RvT were identified and quantified using LC-MS-MS based lipid mediator profiling. * $p<0.05$ and ** $p<0.01$ vs. atorvastatin or pravastatin alone using one-way ANOVA with post hoc Sidak's multiple comparisons test. (D) Representative H&E-stained knee sections of mice (×4 magnification) collected on day 8 using EVOS FL imaging system. Results are mean±s.e.m.; n=9 for vehicle, 11 for atorvastatin, 11 for pravastatin, 7 for celecoxib plus atorvastatin and 6 for celecoxib plus pravastatin treated mice per group from 2-3 independent experiments.

Clinical scores of mice given celecoxib, a COX-2 selective inhibitor, immediately prior to atorvastatin were similar to those of mice receiving vehicle alone and higher than those of mice receiving atorvastatin (FIG. 6A).

Figure 6B:
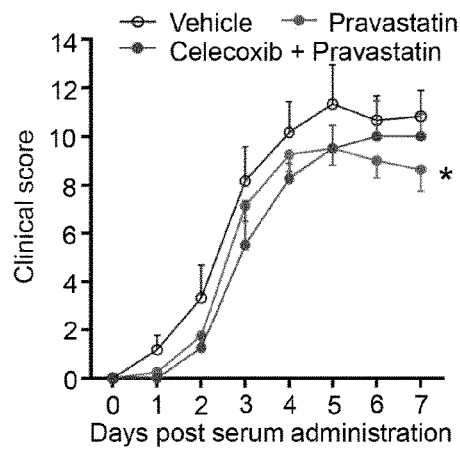

Similarly, celecoxib also blunted the anti-inflammatory actions of pravastatin measured by an increase in disease activity when compared with mice receiving the statin alone (FIG. 6B).

Figure 6C:
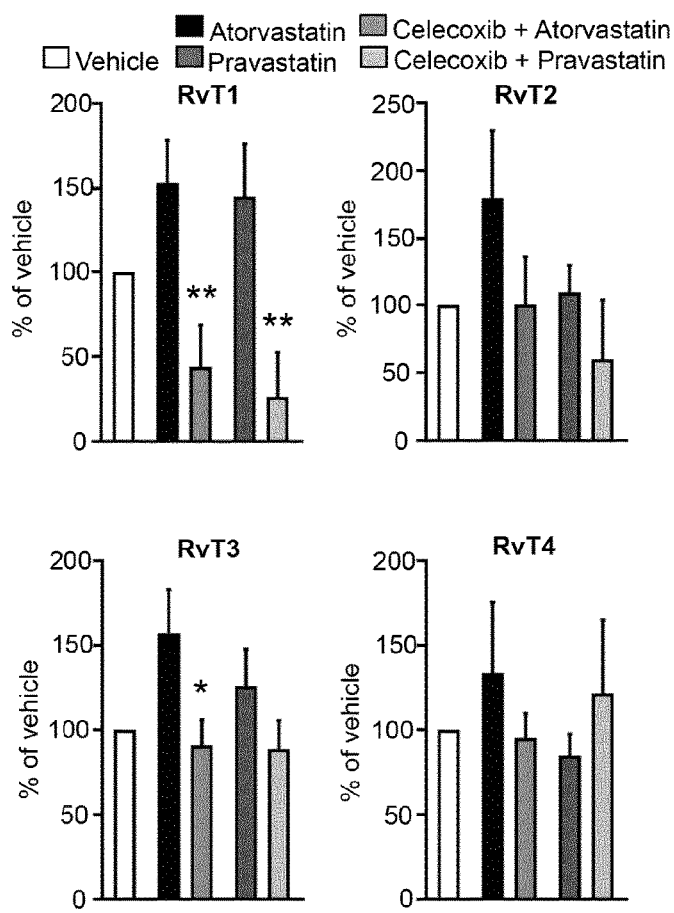

This loss of protective actions of pravastatin and atorvastatin in mice given celecoxib was also associated with an ~60% reduction in joint RvT and a reduction in RvT1 concentration that was >75% when compared to mice given pravastatin or atorvastatin alone (FIG. 6C).

Figure 6D:
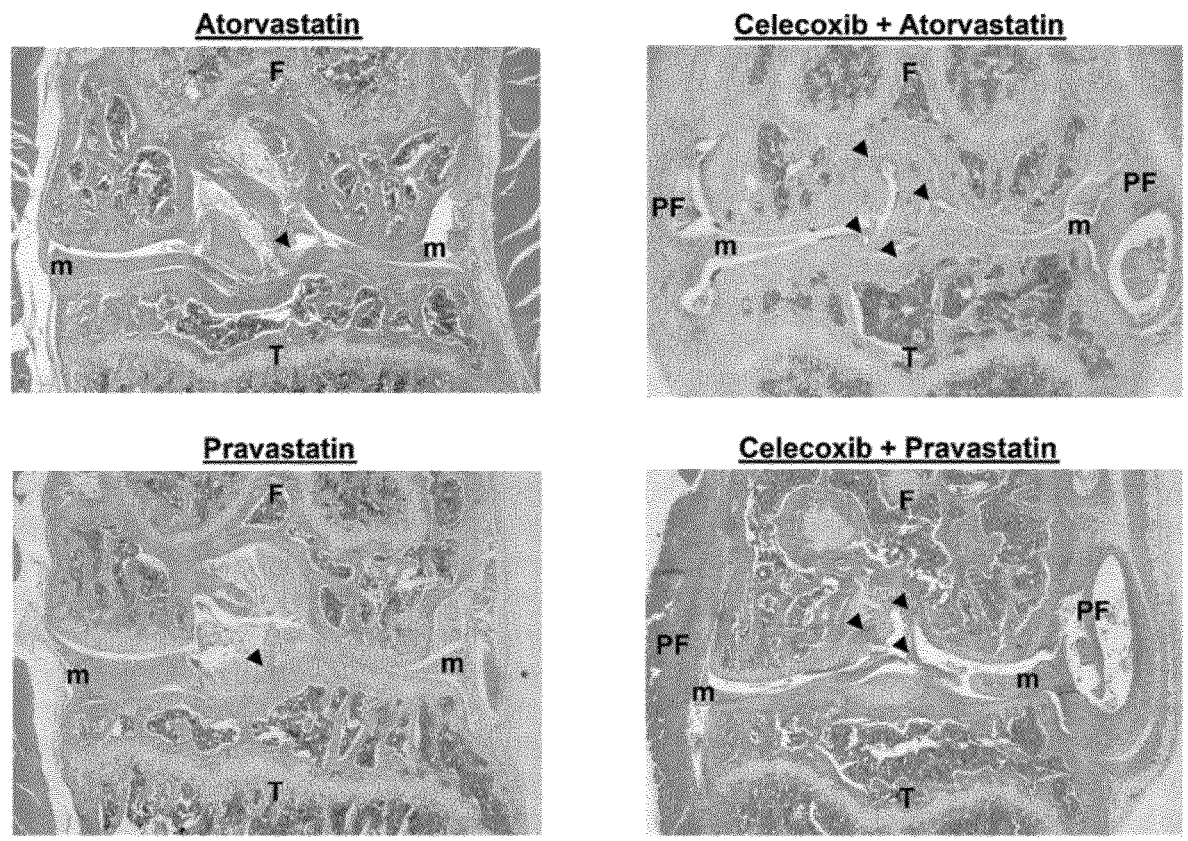

In these mice, a significant reversal of the joint protective actions of both statins was also found where in mice given celecoxib there was an increase in pannus formation and loss of joint architecture when compared to mice given each of the statin alone (FIG. 6D).

It was next investigated whether COX-2 inhibition also reversed the leukocyte directed actions exerted by atorvastatin and pravastatin.

Figures 7A, 7B, 7C, 7D, 7E, 7F:
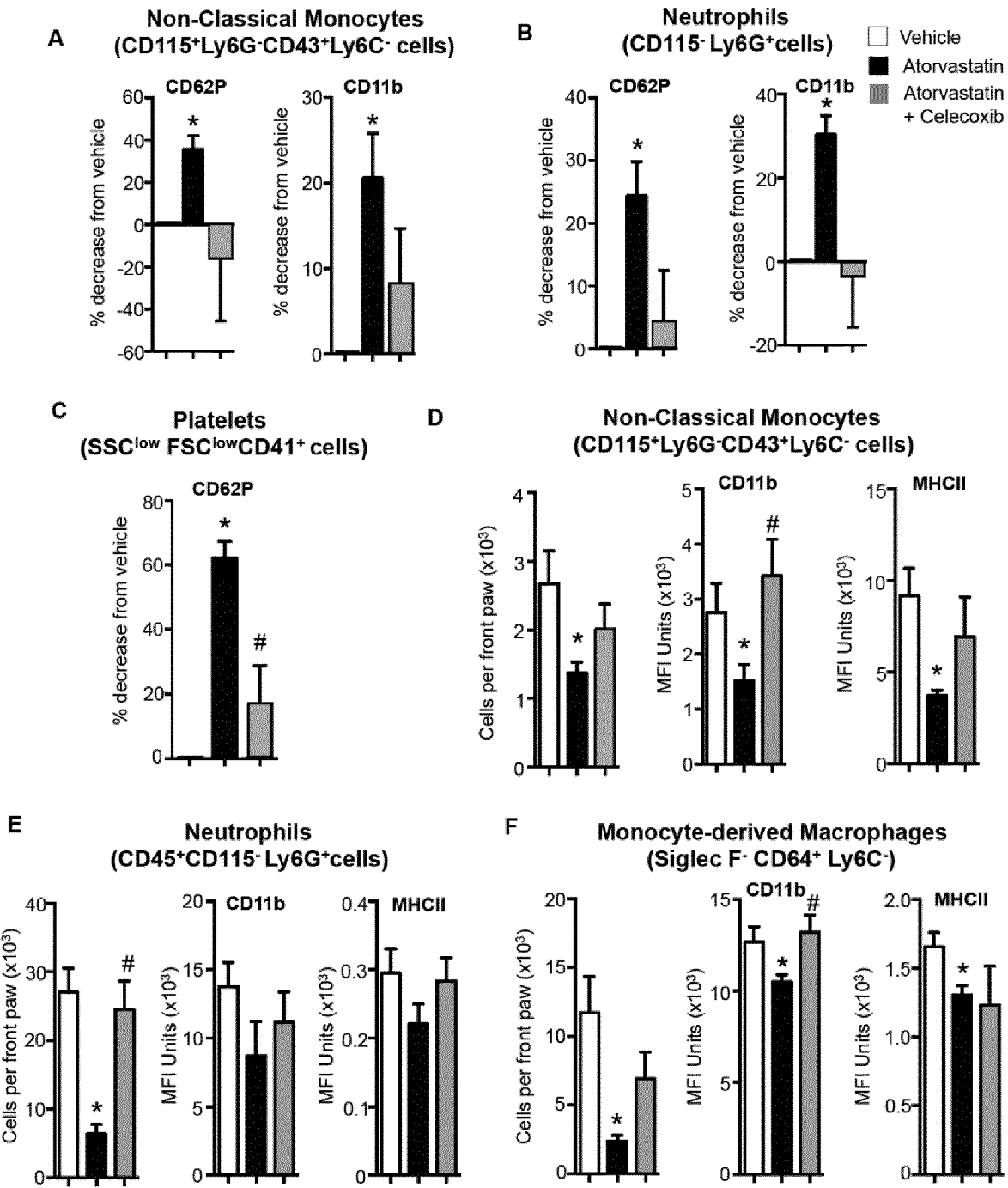
FIGS. 7A-7F: COX-2 inhibition reverses the protective actions of atorvastatin on both systemic and joint leukocytes. Serum-induced arthritis was initiated, on days 3, 5 and 7 and mice were administered celecoxib (10 mg/Kg) or vehicle (DPBS containing 0.05% ethanol) and after 1 hour given atorvastatin (0.2 mg/Kg) or vehicle (DPBS containing 0.05% ethanol). Blood was collected on day 8 and leukocyte subsets and activation were identified using fluorescently labelled antibodies and flow cytometry. (A-C) Activation markers on circulating (A) non-classical monocytes, (B) neutrophils and (C) platelets. Results are presented as percentage decrease from vehicle. (D-F) Leukocytes recovered from the inflamed paws (see methods for details) on day 8. Trafficking and activation profile for (D) non-classical monocytes (E) neutrophils, and (F) monocyte-derived macrophages were assessed using flow cytometry. Results are mean±s.e.m.; n=9 for vehicle, 11 for atorvastatin, 11 for pravastatin, 7 for celecoxib plus atorvastatin treated mice from 2 independent experiments. * $p<0.05$ vs. vehicle; #$p<0.05$ vs atorvastatin using one-way ANOVA with post hoc Dunnett's multiple comparisons test.

Celecoxib administration blunted the protective actions of atorvastatin on circulating leukocytes and platelets, increasing blood platelet-monocyte and platelet-neutrophil aggregates as well as the expression of CD11b on both leukocyte subsets (FIGS. 7A and B). Celecoxib administration also increased the expression of CD62P on circulating platelets when compared to mice receiving atorvastatin alone (FIG. 7C). Inhibition of COX-2 reversed the actions of atorvastatin on leukocyte trafficking and activation in the joint, increasing the numbers of non-classical monocytes (FIG. 7D), neutrophils (FIG. 7E) and monocyte-derived macrophages (FIG. 7F) recruited to the inflamed joints. Expression of activation markers on these leukocytes was also increased following celecoxib inhibition when compared with mice given atorvastatin alone (FIGS. 7D-F).

Similar findings were also made when systemic and joint leukocyte responses and trafficking in mice given celecoxib together with pravastatin were assessed. Here it was found that COX-2 inhibition returned the activation profile of circulating leukocytes and platelets to that observed in mice receiving vehicle alone. Similarly, leukocyte trafficking and activation in the joints was increased to levels that were similar to those found in vehicle treated mice.

Together these findings demonstrate that inhibition of COX-2 reduces RvT production and abolished the joint and systemic protective actions of pravastatin and atorvastatin in inflammatory arthritis.

These results demonstrate that both atorvastatin and pravastatin increase RvT production in inflammatory arthritis. Upregulation in tissue and blood concentrations of these SPM was associated with a reduction in joint disease activity as well as joint leukocyte trafficking and activation. In addition, both atorvastatin and pravastatin also decreased systemic inflammation reducing platelet, monocyte and neutrophil activation. The protective actions of these statins were reversed by inhibition of COX-2. Of note, simvastatin did not increase RvT and displayed blunted actions in regulation of joint disease and leukocyte responses.

Together these findings establish the rank order potency of atorvastatin, pravastatin and simvastatin in regulating RvT and the role of these molecules in mediating the protective actions of these statins. Joint and systemic increases in these pro-resolving mediators also correlated with the ability of each of these three statins to dampen various aspects of local and systemic inflammation including oedema, leukocyte and platelet activation. Thus, these results establish a novel mechanism of action for atorvastatin and pravastatin in regulating inflammation in arthritis and provide novel functional biomarkers for measuring the efficacy of statins in controlling local and vascular inflammation in patients.

Example 2

Figure 8:
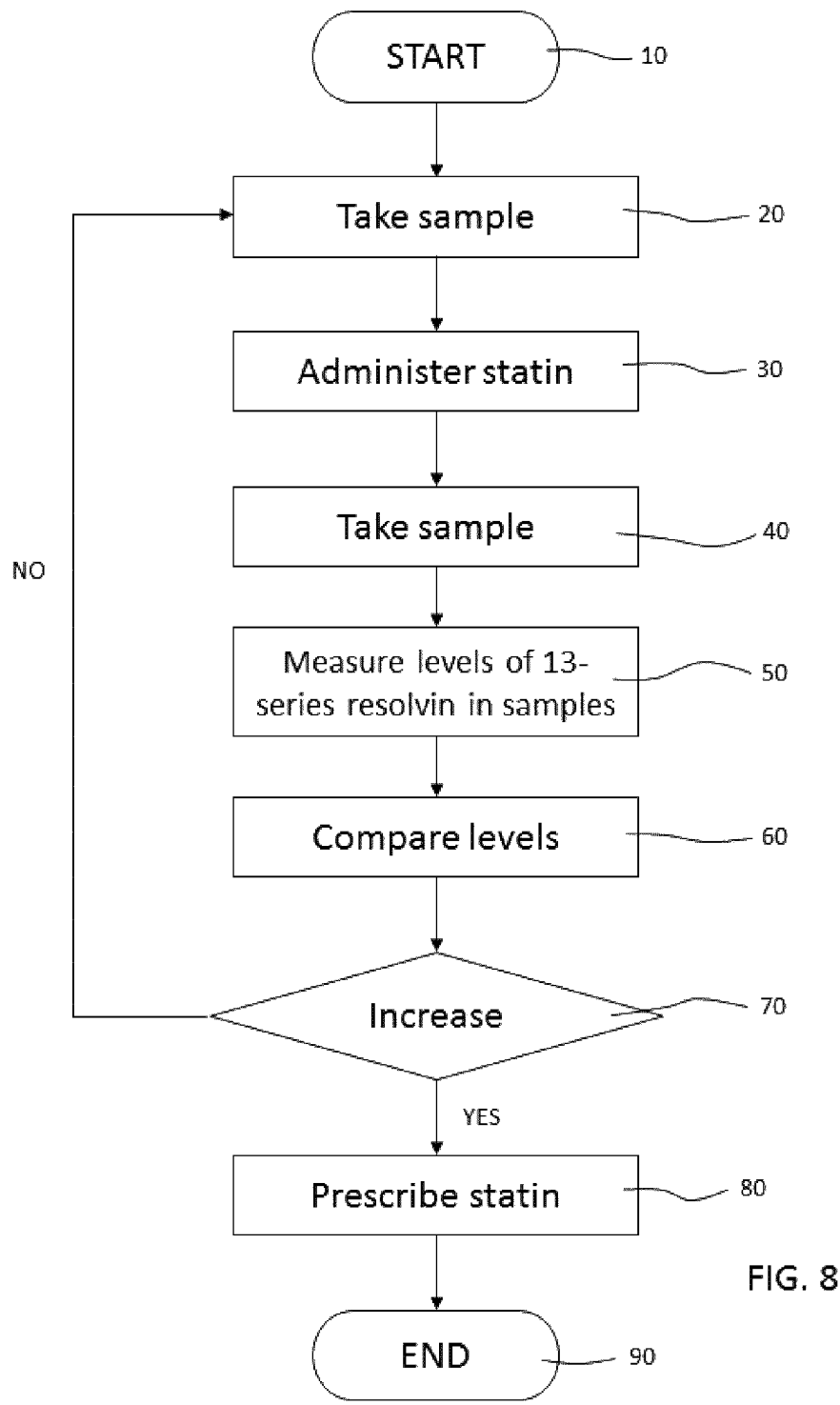
FIG. 8 is a flow diagram illustrating an example of a method of assessing the efficacy of a statin (atorvastatin) for treating inflammation in an individual patient in accordance with the present invention.

A method of assessing the efficacy of a statin for use in the treatment of an inflammatory condition in an individual patient in accordance with the present invention is illustrated in FIG. 8.

Step 10 indicates the start of the method. First, a first suitable biological sample is taken from the patient (step 20). In the present example, the biological sample is a plasma sample, but in other embodiments, the sample may be whole blood or serum taken from the patient, or a suitable tissue sample.

An amount of the statin to be tested is then administered to the patient (step 30). In accordance with the invention, any statin that is approved for use, either for marketing as a medicinal product or for use as investigational medicinal product (IMP) in clinical studies, may be administered. The statin may be administered according to its recommended initial or maintenance dose. Suitably, the statin may be administered according to its recommended initial dose. In the present example, atorvastatin is used at a dose of 10 mg or 20 mg. However, in other embodiments, a different statin may be used. The amount administered to the patient may be adjusted in accordance with clinical practice.

After a prescribed period of time, a second biological sample is taken from the patient (step 40). In the present example, the prescribed period of time is 2-3 hours, but again, other time periods may be used in different embodiments. The period of time should be sufficiently long to allow the pharmacological effects of the statin to manifest themselves.

In step 50, the first and second samples taken from the patient in steps 20 and 40, before and after administration of the statin, are analysed to quantify the levels of at least one 13-series resolvin (RvT) in the samples. In the present example, the levels of four 13-series resolvins (RvT1, RvT2, RvT3 and RvT4) are measured in the first and second samples by reverse phase liquid chromatography electrospray tandem mass spectrometry (LC-MS/MS). In different embodiments of the invention, fewer than four of the 13-series resolvins may be analysed, i.e. one, two or three of the 13-series resolvins. Details of this method of quantitating the levels of the 13-series resolvins in the first and second samples are disclosed in Colas R A et al. 2014 (ibid) and Dalli et al. 2015 (ibid), the contents of which are incorporated herein by reference.

For each of the first and second plasma samples, venous blood (10 mL) is collected in heparin from the patient. Plasma is obtained by centrifugation of heparinised blood (2000 g, 10 minutes) and placed in 4 volumes of methanol before solid-phase extraction as described below.

Internal labelled standards 5S-HETE-$d_8$, LTB$_4$-$d_4$, LXA$_4$-$d_5$, RvD2-$d_5$ and PGE$_2$-$d_4$ (500 pg each) in 4 mL of ice-cold methanol are added to each sample to facilitate quantification and sample recovery. Next, samples are held at −20° C. For 45 minutes to allow protein precipitation and then centrifuged (2000 g, 4° C., 10 minutes). Supernatants are collected and brought to less than 1 mL of methanol content in a gentle stream of nitrogen onto an automated evaporation system with the water bath set to 37° C. and a nitrogen feed with a flow rate of no more than 15 psi. The samples are then centrifuged (2000 g, 4° C., 10 minutes). Samples are then placed in an automated extraction system with the water bath set to 37° C. and a nitrogen feed with a flow rate of no more than 15 psi and products extracted as follows.

Solid-phase C18 cartridges are washed with 3 mL of methanol and 6 mL of H$_2$O. 9 mL H$_2$O (pH 3.5, HCl) is then added to the samples, and the acidified solutions are rapidly loaded onto the conditioned C18 columns that are washed with 4 mL of H$_2$O to neutralise the acid. Next, 5 mL of hexane are added and the products are eluted with 9 mL methyl formate. Products are brought to dryness using the automated evaporation system and immediately suspended in methanol-water (50:50 vol/vol) for LC-MS/MS automated injections.

In the present example, for LC-MS/MS, an HPLC and autoinjector, paired with a triple quadrupole mass spectrometer fitted with a high dynamic range pulse counting system, is employed. Alternative suitable LC-MS/MS equipment is available to those skilled in the art. A C18 column is kept in a column oven maintained at 50° C., and the RvT lipid mediators are eluted with a mobile phase consisting of water containing 0.01% acetic acid as a solvent A and methanol containing 0.01% acetic acid as solvent B. The column is equilibrated with mobile phase at 80:20 (A:B) which is ramped to 50:50 (A:B) over 12 seconds. This gradient is maintained for two minutes and then ramped to 80:20 (A:B) over the next 9 minutes. This gradient is then maintained for the next 3.5 minutes, before ramping to 98:2 (A:B). Finally, this gradient is maintained for 5.4 minutes to wash the column. The flow rate is maintained at 0.5 mL/min throughout the process.

The mass spectrometer is operated in negative ionisation mode using scheduled multiple reaction monitoring (MRM) coupled with information-dependent acquisition and an enhanced product line scan. The scheduled MRM window is 90 seconds, and each lipid mediator parameter is optimised individually.

The identity of each RvT (13-series resolvin) is confirmed by matching its retention time ($R_T$) to synthetic and authentic materials (FIG. 1B) and at least six diagnostic ions for each RvT (FIG. 1C) and quantified using multiple reaction monitoring of the parent ion (Q1) and characteristic daughter ion (Q3) as described in Table 2 below.

TABLE 2

| RvT | Q1 | Q3 |
| --- | --- | --- |
| RvT1 | 377 | 193 |
| RvT2 | 377 | 215 |
| RvT3 | 377 | 143 |
| RvT4 | 361 | 193 |

Calibration curves are obtained for each using authentic compound mixtures and deuterium labelled lipid mediators at 3.12, 6.25, 12.5, 25, 50, 100 and 200 pg. Linear calibration curves are obtained for each LM, which gives $r^2$ values of 0.98-0.99. Internal standard recoveries, interference of the matrix, and limit of detection are determined.

Following quantitation of the levels of the RvTs in each of the first and second samples, the levels are compared (step 60).

A significant increase in the levels of the RvTs in the second sample as compared to the first sample indicates that the statin administered to the patient may be effective in controlling inflammation. On the other hand, no increase in the levels of the RvTs in the second sample as compared with the first sample may indicate that the administered statin is ineffective in the individual patient (step 70).

Based on these results, the statin may be prescribed to the patient if it is indicated as being effective (step 80). Alternatively, the method may be repeated, e.g., the following day, using a different statin.

Step 90 indicates the end of the method.

Example 3

Figure 9:
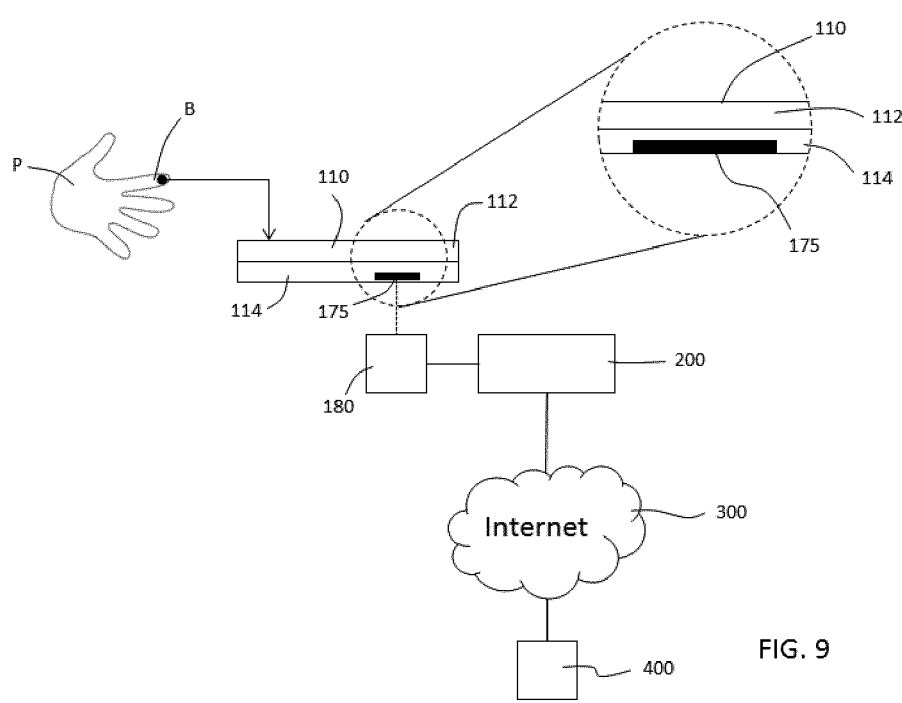
FIG. 9 is a schematic diagram of apparatus for carrying out methods of the present invention using a microfluidic device to carry out an immunoassay.

Further examples of different aspects of the present invention are described below with reference to FIGS. 9 and 10 in which an immunoassay incorporated into a microfluidic device 110 is used for measuring the level of at least one 13-series resolvin (RvT) in a sample of blood B obtained from a patient P.

Figure 10:
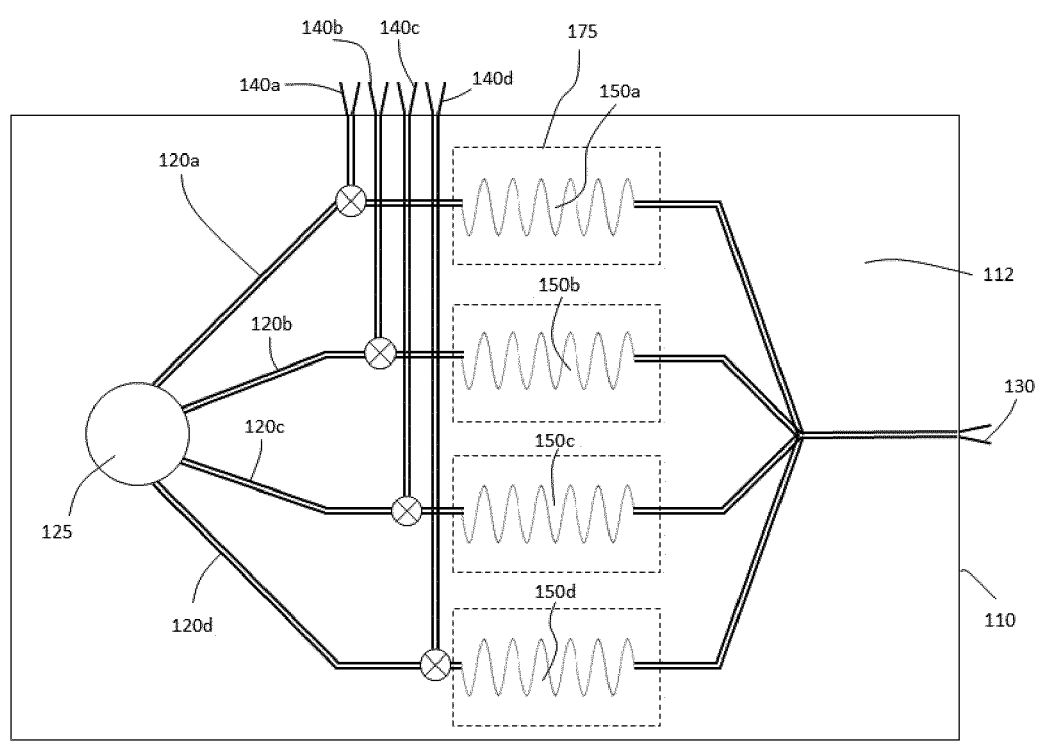
FIG. 10 is a schematic diagram of a microfluidic device according to the present invention which incorporates an immunoassay of the invention.

As best shown in FIG. 10, the microfluidic device 110 has a general construction of the kind known to those skilled in the art. Specifically, the microfluidic device 110 comprises at least one layer of polydimethylsiloxane (PDMS) 112, a transparent, biocompatible elastomer that allows for channel inspection and optical signal acquisition, bonded to a glass slide 114.

The PDMS layer is moulded with a plurality of micro-channels 120*a-d* which terminate at one end at a sample collector port 125 and at another end at a waste drain 130. In the present example, the microfluidic device 110 has four micro-channels 120*a-d*, one for measuring the level of a different respective RvT (RvT1, RvT2, RvT3, RvT4) in the blood sample B. As in Example 2 above, in variants of the present example, the microfluidic device may have fewer than four micro-channels, for instance one, two or three micro-channels for measuring the levels of a corresponding number of RvTs.

Between the sample collector port 125 and the waste drain 130, each of the micro-channels 120*a-d* comprises a reaction zone 150*a-d*. Suitably, the micro-channels 120*a-d* may be serpentine in the reaction zone 150*a-d* to promote mixing of the sample B and reagents added to the device as described below.

Intermediate the sample collection port 125 and its reaction zone 150*a-d*, each microchannel 120 *a-d* is provided with a respective reagent inlet port 140*a-d* for admitting a series of different reagents into the channels 120*a-d* for mixing with the sample B. The micro-channels 120*a-d* and inlet ports 140*a-d* are provided with suitable micro-valves or the like for controlling the flow of the sample and reagents.

In each reaction zone 150*a-d*, a surface of each micro-channel 120*a-d* is coated with a monoclonal antibody to a different respective one of RvTs to be quantitated in the sample B.

Adjacent each reaction zone 150*a-d*, the device 110 incorporates hydrogenated amorphous silicon (a-Si:H) photodiodes 175*a-d* on the glass slide 114. The photodiodes 175*a-d* are connected to a suitable interface 120, which is connected to a first computer 200. The interface 120 is arranged to receive signals from the photodiodes 175*a-d* and to transmit computer-readable data to the first computer 200 representing those signals. The interface 120 may be physically connected to the first computer 200 by a suitable data cable. Alternatively, the interface 120 may be connected wirelessly to the first computer 200 by any suitable wireless data transfer method such, for example, as Bluetooth®. In some embodiments, the first computer may comprise a handheld device.

The first computer 200 comprises a microprocessor, a memory and a storage device, and is arranged to execute software for storing data representing the signals received from the photodiodes 175*a-d* in association with patient identity data. Where the first computer 200 is a handheld device, the software may be an app.

The first computer 200 is connected via a suitable data communication channel 300 to a remote second computer 400. In the present embodiment, the data communication channel 300 comprises the Internet, but in other embodiments, the first and second computers 200, 400 may be interconnected on a local or wide area network (not shown). The first and second computers 200, 400 may be physically to each other connected via data communication cables, or they may be interconnected wirelessly using a suitable wireless data communication technology such, example, as IEEE 802.11 a,b,g,n or Bluetooth®. Suitably, each of the first and second computers 200, 400 is connected to the Internet 300 through a suitable modem.

In use, a sample of blood B is obtained from a patient, for example using a conventional lancet. The sample B is placed on the microfluidic device 110 at the sample inlet port 125. The sample is drawn into the micro-channels 120*a-d* by capillary action. In alternative embodiments, the sample B may be actively drawn into the micro-channels 120*a-d* using a micro-pump or under reduced pressure, etc.

In the reaction zones 150*a-d*, RvTs in the samples react with the antibodies coated on the surface of the micro-channels 120*a-d*. A different RvT is captured in each reaction zone 150*a-d*. The sample B is incubated with the antibodies in the reaction zone for a suitable period of time.

A wash solution is then introduced into the micro-channels 120*a*-*d* to remove unbound sample. Discarded material from the micro-channels 120*a*-*d* is removed from the device 110 via the drain 130.

After removing unbound sample from the reaction zone 150*a*-*d*, a second monoclonal antibody is introduced into each of the micro-channels 120*a*-*d* with specificity for the respective RvT. Each of the second antibodies is tagged with horseradish peroxidase in the manner well known to those skilled in the art. The second monoclonal antibodies are allowed to incubate with the surface-captured RvTs in the reaction zones 150*a*-*d*. The micro-channels 120*a*-*d* are then washed again.

Next, a substrate for horseradish peroxidase is introduced into each of the micro-channels 120*a*-*d* via the inlet ports 140*a*-*d*. Suitable substrates are known to those skilled in the art, but in the present example luminol is used, which fluoresces when acted on by horseradish peroxidase. The fluorescence is detected by the photodiodes 175 giving rise to signals that are received by the interface 180. The intensity of the fluorescence is indicative of the amount of second antibody that is bound to the immobilised RvT in each of the channels 120*a*-*d*. The microfluidic device 110 may be calibrated in a manner known to those skilled in the art so that the level of RvT in each of the micro-channels 120*a*-*d* can be quantitated.

Data representing the intensity of fluorescence in each microchannel 120*a*-*d* is transmitted from the interface 180 to the first computer 200 as described above. The computer 200 executes the aforementioned software to calculate the level of each RvT in the sample B from the intensity of fluorescence measured by the photodiodes 175.

The microfluidic device is then washed through again with a suitable washing agent.

As described above in Example 2, a statin is then administered to the patient P. Suitably, the statin is administered according to its recommended initial or maintenance dose. Since details of administration of the statin have been described above, they are not repeated here.

After a suitable period of time—for example 2-3 hours—a second sample B is obtained from the patient P and tested using another microfluidic device 110 that is similar to the one described above. The levels of the RvTs in the second sample are measured in the same way, and data representing the levels are calculated and stored by the first computer 200.

Data representing the levels of RvTs in the first and second samples are then transmitted by the first computer 200 to the second computer 400 in association with information identifying the patient P.

The second computer 400 includes a microprocessor, memory and a storage device and is arranged to execute software for comparing the levels of the RvTs in the first and second samples to determine whether or not the levels of RvTs in the second sample are increased (by a biologically relevant amount) as compared with the levels in the first sample. If the levels of the RvTs are increased in the second sample relative to the first sample, the statin is assessed to be effective for treating an inflammatory disorder in the patient P, and data indicating this is transmitted from the second computer back to the first computer 200 where it is saved and/or displayed to a person carrying out the test. On the basis of the result of the comparison of the RvT levels in the first and second samples, the patient may be prescribed the statin. On the other hand, if the levels of RvTs in the second sample are not significantly increased relative to the levels in the first sample, the statin is assessed to be ineffective in the patient P for treating inflammatory condition. The test may then be repeated, e.g., the next day, with a different statin.

In the present example, the microfluidic device 110 is arranged to carry out a non-competitive, heterogeneous ELISA sandwich immunoassay. However, in variants of the invention, a microfluidic device may be arranged to carry out a homogeneous immunoassay and/or a competitive immunoassay.

For example, in one variant, each microchannel 120*a*-*d* may be coated on a surface within its respective reaction zone 150*a*-*d* with a respective RvT (i.e. RvT1, RvT2, RvT3 or RvT4) which is the same as the one in the sample B that is to be analysed in the respective reaction zone 150*a*-*d*. Intermediate the reaction zone 150*a*-*d* and the sample collection port 125, in each microchannel 120*a*-*d* the sample B may be mixed with a known amount of a primary antibody to the respective RvT. The primary antibody is provided in excess, and remaining antibody will then subsequently react with the surface-bound RvT in the reaction zone 150*a*-*d*, effectively in competition with the corresponding RvT in the sample. After washing, a labelled secondary antibody is introduced into each reaction zone 150*a*-*d* through the inlet ports 140*a*-*d* which is specific for the respective primary antibody. As described above, the secondary antibody is tagged with an enzyme suitable for use in EIA such, for example, as horseradish peroxidase. The amount of secondary antibody remaining after reaction with the sample can then be measured by admitting a suitable substrate for horseradish peroxidase into the reaction zones 150*a*-*d* and measuring the intensity of the fluorescence or colour as described above.

A microfluidic device in accordance with the invention such, for example, as microfluidic device 110 described above provides a convenient device for performing the methods of the present invention in a point of care setting such, for example, as a healthcare clinic where there is no access to more sophisticated equipment such as LC-MS/MS which may only be found in large laboratories.

Example 4: Methods for Enhancing the Stability of Lipid Mediators

Figure 11:
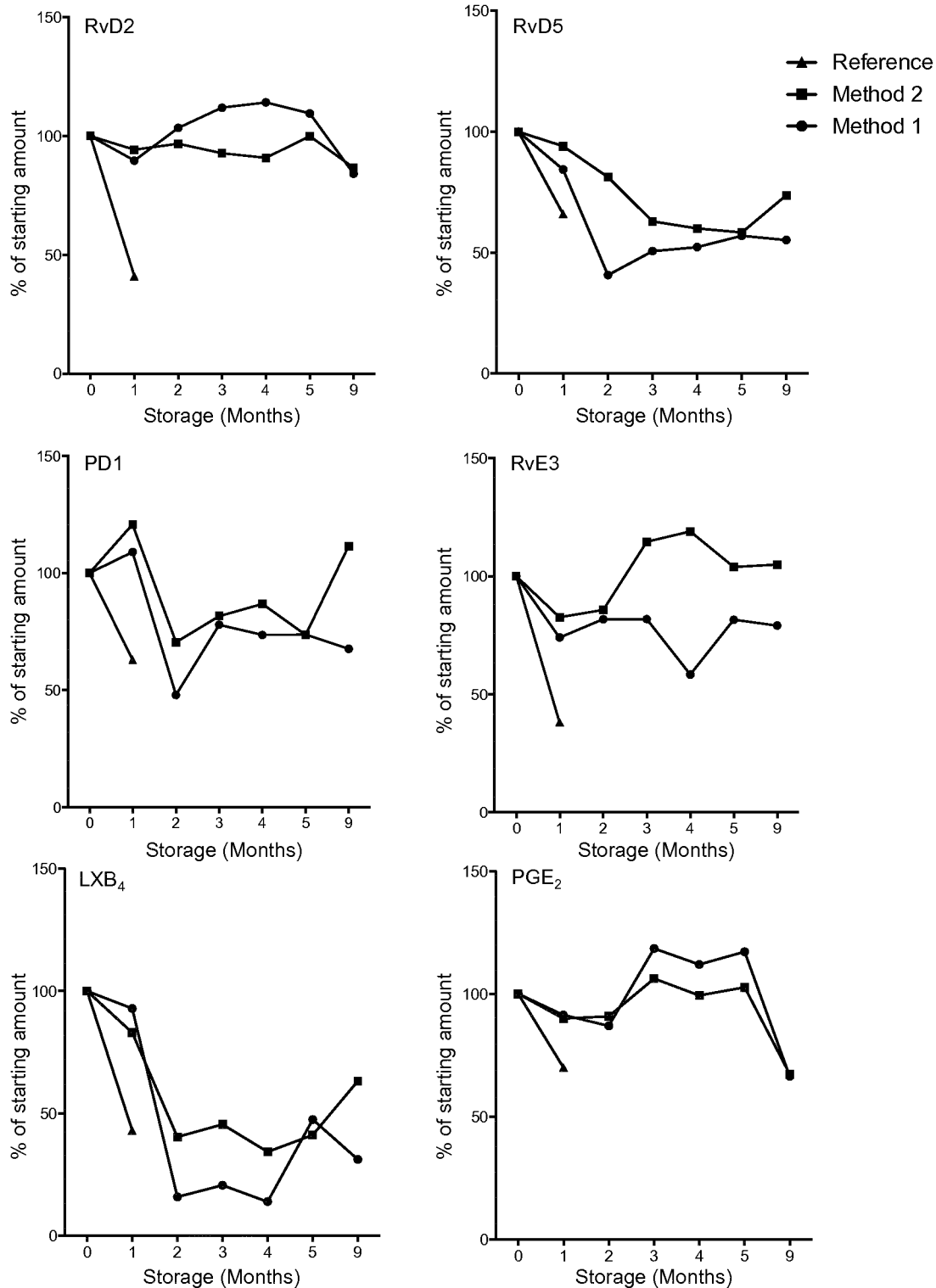
FIG. 11 shows the results of experiments comparing the stability of lipid mediators over extended periods of time when stored at −80° C. under nitrogen and methanol respectively.

Human serum was either snap frozen and stored under nitrogen (Method 1 below) or placed in methanol containing deuterium labelled internal standards (Method 2). At the intervals indicated in FIG. 11, lipid mediators were extracted, and the concentrations of the indicated products were determined. These were then compared to published values (reference) were samples were only snap frozen without additional treatment. Results are mean of n=1 experiment and 3 determinations and are illustrated in FIG. 11.

Method 1
a) Prepare serum following appropriate methods
b) Collect serum and transfer to appropriate container.
c) Purge tube with nitrogen for an appropriate amount of time to replace air in the headspace above the serum with nitrogen. Note: This step needs to be performed immediately after sample collection and without exposing samples to temperatures above room temperature.
d) Immediately snap-freeze the sample by placing in liquid nitrogen until frozen.
e) Transfer tubes to appropriate container and store at −80° C. or lower. Note: Samples should not be thawed and refrozen at any point.

Method 2
a) To prepare methanol for each 1 mL of serum add 500 pg of each of the deuterium labelled internal standards to 4 ml of mass spectrometry grade methanol.
b) Store at −20° C. for at least 1 h prior to use.
c) Prepare serum following appropriate methods.
d) Collect serum and transfer to appropriate container.
e) Add 4 mL of methanol containing deuterium labelled internal standards per 1 mL of serum
f) If samples are to be immediately processed these should be placed at −20° C. for at least 45 min prior to lipid mediator extraction
g) If samples are to be stored these should be stored at −80° C. or lower.

REFERENCE METHOD

Colas R A et al. 2014 (ibid).

The invention claimed is:

1. A method of treating an inflammatory condition in a patient with a statin, the method comprising assessing the efficacy of the statin for use in the treatment of the inflammatory condition in the patient wherein the inflammatory condition is cardiovascular disease (CVD) or rheumatoid arthritis, wherein said assessing comprises measuring the levels of at least one 13-series resolvin in biological samples obtained from the patient before and after administration of the statin, wherein an increase in the level of the resolvin after administration of the statin is indicative of efficacy of the statin, and administering the statin to the patient.

2. A method as claimed in claim 1, wherein the at least one 13-series resolvin is selected from RvT1 (7,13,20-trihydroxy-8,10,14,16Z,18-docosapentaenoic acid), RvT2 (7,12,13-trihydroxy-8,10,14,16Z,19Z-docosapentaenoic acid), RvT3 (7,8,13-trihydroxy-9,11,14,16Z,19Z-docosapentaenoic acid) and RvT4 (7,13-dihydroxy-8,10,14,16Z,19Z-docosapentaenoic acid).

3. A method as claimed in claim 2, wherein the levels of two or more of the 13-series resolvins in the biological samples are measured.

4. A method as claimed in claim 2, wherein the levels of three or all four of the 13-series resolvins in the biological samples are measured.

5. A method as claimed in claim 1, wherein the samples are blood, serum or plasma samples.

6. A method as claimed in claim 1, wherein the levels of the at least one 13-series resolvin in the samples are measured using liquid chromatography tandem mass spectrometry (LC-MS/MS).

7. A method as claimed in claim 6, wherein one or more internal labelled standards are added to the samples and quantitation is carried out using linear regression curves constructed using said one or more labelled standards.

8. A method as claimed in claim 1, wherein the levels of the at least one 13-series resolvin in the samples are measured using an immunoassay.

9. A method as claimed in claim 8, wherein the immunoassay is an enzyme immunoassay (EIA).

10. A method as claimed in claim 8, wherein the immunoassay is competitive or non-competitive.

11. A method as claimed in claim 1, wherein the statin is selected from atorvastatin, cerivastatin, fluvastatin, lovastatin, mevastatin, pitavastatin, pravastatin, rosuvastatin and simvastatin.

12. A method as claimed in claim 1, wherein the sample obtained from the patient after administration of the statin is taken at least 30 minutes after administration of the statin.

* * * * *